US008585778B2

(12) United States Patent
Fadli

(10) Patent No.: US 8,585,778 B2
(45) Date of Patent: Nov. 19, 2013

(54) CATIONIC 6-AMINOINDOLINES, DYEING COMPOSITIONS CONTAINING THEM, PROCESSES AND USES THEREOF

(75) Inventor: Aziz Fadli, Chelles (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/582,721

(22) PCT Filed: Mar. 2, 2011

(86) PCT No.: PCT/EP2011/053081
§ 371 (c)(1),
(2), (4) Date: Dec. 17, 2012

(87) PCT Pub. No.: WO2011/107501
PCT Pub. Date: Sep. 9, 2011

(65) Prior Publication Data
US 2013/0081213 A1 Apr. 4, 2013

Related U.S. Application Data

(60) Provisional application No. 61/318,970, filed on Mar. 30, 2010.

(30) Foreign Application Priority Data

Mar. 2, 2010 (FR) ..................................... 10 51499

(51) Int. Cl.
*A61Q 5/10* (2006.01)
*C07D 209/00* (2006.01)
(52) U.S. Cl.
USPC ................ 8/405; 8/406; 8/408; 8/435; 8/574; 548/490

(58) Field of Classification Search
USPC ............... 8/405, 406, 408, 435, 574; 548/490
See application file for complete search history.

(56) References Cited

FOREIGN PATENT DOCUMENTS

WO    WO 2008/039087 A2 * 3/2008

OTHER PUBLICATIONS

STIC Search Report dated Mar. 21, 2013.*

* cited by examiner

*Primary Examiner* — Eisa Elhilo
(74) *Attorney, Agent, or Firm* — John A. Artz; Dickinson Wright PLLC

(57) ABSTRACT

The present invention relates to a cationic 6-aminoindoline of general formula (I), the addition salts thereof with an acid and the solvates thereof: the present invention is also directed towards a method for synthesizing this cationic 6-aminoindoline, the compositions, the uses, the hair dyeing methods and the devices using this cationic 6-aminoindoline.

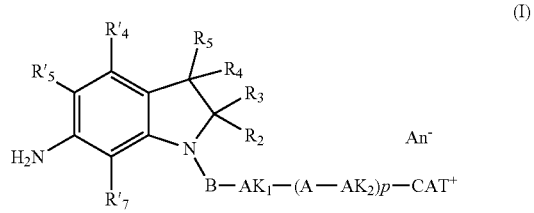

15 Claims, No Drawings

CATIONIC 6-AMINOINDOLINES, DYEING COMPOSITIONS CONTAINING THEM, PROCESSES AND USES THEREOF

This application is a national phase application based on PCT/EP2011/053081 filed Mar. 2, 2011, which claims priority from French Applications No. 1051499, filed Mar. 2, 2010, and claims the benefit of U.S. Provisional Application No. 61/318,970, filed on Mar. 30, 2010, the content of all of which is incorporated herein by reference in their entirety.

TECHNICAL FIELD

The subject matter of the present application is novel cationic 6-aminoindolines, the use thereof for dyeing keratin fibres, in particular human keratin fibres such as the hair, the dyeing compositions comprising such cationic 6-aminoindolines and also the methods and devices using these cationic 6-aminoindolines.

BACKGROUND

It is known practice to dye keratin fibres, and especially human hair, with dyeing compositions containing oxidation dye precursors, generally called oxidation bases, such as ortho- or para-phenylenediamines, ortho- or para-aminophenols and heterocyclic compounds. These oxidation bases are colourless or weakly coloured compounds which, when combined with oxidizing products, are able to produce coloured compounds by a process of oxidative condensation.

It is also known that the shades obtained with these oxidation bases can be varied by combining them with couplers or coloration modifiers, the latter being selected more particularly from aromatic meta-diaminobenzenes, meta-aminophenols, meta-diphenols and certain heterocyclic compounds such as indole compounds.

The variety of molecules used as oxidation bases and couplers allows a wide range of colours to be obtained.

The "permanent" coloration obtained by virtue of these oxidation dyes is required, moreover, to meet a certain number of demands. Thus it should have no toxicological drawbacks, it should allow shades to be obtained in the desired intensity, and it should be highly resistant to external agents such as light, bad weather, washing, permanent wave treatments, perspiration and rubbing.

The dyes must also allow grey hair to be covered, and they must be as unselective as possible, i.e. they must make it possible to produce the smallest possible colouration differences along the same lock of keratin fibre, which is generally differently sensitized (i.e. damaged) between its end and its root.

SUMMARY OF THE INVENTION

Surprisingly and advantageously, the Applicant has just discovered a novel family of heterocyclic couplers formed from cationic 6-aminoindolines. These couplers make it possible to produce novel compositions for dyeing keratin fibres, which are capable of giving colourations in varied, powerful, chromatic shades.

These compositions are also sparingly selective and are resistant: they show good resistance to various attacking factors to which the fibres may be subjected.

Moreover, these heterocyclic couplers show good solubility, allowing satisfactory uptake of the colour.

A first subject of the invention relates to a family of cationic 6-aminoindolines and methods for synthesizing them.

A subject of the invention is also a composition containing at least one cationic 6-aminoindoline, the dyeing methods using this composition, the uses of said composition according to the present invention for dyeing keratin fibres, in particular human keratin fibres such as the hair, and in particular multi-compartment dyeing devices or "kits".

Other features, aspects, objects and advantages of the present invention will emerge even more clearly from a reading of the description and examples which follow.

DESCRIPTION OF THE PREFERRED EMBODIMENTS

The present invention relates to a cationic 6-aminoindoline of general formula (I), the addition salts thereof with an acid and the solvates thereof:

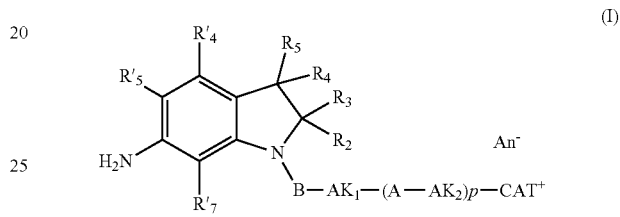

(I)

in which:
B denotes a covalent bond or a carbonyl radical CO;
$AK_1$ and $AK_2$ independently denote a linear or branched, saturated $C_1$-$C_{10}$ hydrocarbon-based chain optionally substituted with one or more hydroxyl radicals;
A denotes an oxygen atom or an $NR_6$ radical;
p=0, 1 or 2;
when p is equal to 2, the A radicals may be identical or different and the $AK_2$ radicals may be identical or different;
$CAT^+$ represents a cationic radical selected from:
  a cationic heterocyclic radical optionally substituted with one or more radicals, which may be identical or different, selected from linear or branched $C_1$-$C_4$ alkyl radicals or linear or branched $C_1$-$C_4$ hydroxyalkyl radicals,
  a tri(hydroxy)($C_1$-$C_4$)alkylammonium radical,
  a non-cationic heterocyclic radical comprising from 5 to 8 ring members, substituted with a cationic radical optionally substituted with one or more radicals, which may be identical or different, selected from linear or branched $C_1$-$C_4$ alkyl radicals or $C_1$-$C_4$ hydroxyalkyl radicals.

For the purposes of the present invention, the term "cationic heterocyclic radical" means a heterocyclic radical comprising 5 to 8 ring members, one of the ring members of which is a quaternary ammonium.

Examples of cationic heterocyclic radicals include imidazolium, pyridinium, piperazinium, pyrrolidinium, morpholinium, pyrimidinium, thiazolium, benzimidazolium, benzothiazolium, oxazolium, benzotriazolium, pyrazolium, triazolium, benzoxazolium and piperidinium radicals.

For the purpose of the invention, the term "tri(hydroxy)-($C_1$-$C_4$)alkylammonium radical" means an ammonium group substituted with one or more alkyl and/or hydroxyalkyl radicals. Examples that may be mentioned include trimethylammonium, triethylammonium, dimethylethylammonium, diethylmethylammonium, diisopropylmethylammonium, diethylpropylammonium, beta-hydroxyethyldiethylammonium, dimethyl-beta-hydroxyethylammonium, di-beta-hydroxyethylmethylammonium and tri-beta-hydroxyethylammonium radicals.

Examples of non-cationic heterocyclic radicals comprising from 5 to 8 ring members that may be mentioned include imidazole, pyridine, piperidine, piperazine, pyrrolidine, morpholine, pyrimidine, thiazole, benzimidazole, benzothiazole, oxazole, benzotriazole, pyrazole, triazole and benzoxazole radicals.

For the purpose of the present invention, the term "cationic radical" means a tri(hydroxy)($C_1$-$C_4$)alkylammonium radical, a cationic heterocyclic radical or a $C_1$-$C_4$ alkyl radical substituted with a tri(hydroxy)($C_1$-$C_4$)alkylammonium radical or with a cationic heterocyclic radical.

$R_2$, $R_3$, $R_4$ and $R_5$, independently of one another, are selected from: a hydrogen atom, halogens selected from fluorine, chlorine or bromine, and linear or branched $C_1$-$C_4$ alkyl, carboxyl (—COOH), ($C_1$-$C_4$)alkoxycarbonyl, $C_1$-$C_4$ hydroxyalkyl or ($C_1$-$C_4$)alkoxy($C_1$-$C_4$)-alkyl radicals;

$R'_4$, $R'_5$ and $R'_7$, independently of one another, are selected from: a hydrogen atom, halogens selected from fluorine, chlorine or bromine, and $C_1$-$C_4$ alkyl radicals;

$R_6$ is a hydrogen atom or a linear or branched $C_1$-$C_4$ alkyl radical, a $C_1$-$C_4$ hydroxyalkyl radical, a benzyl radical or an acetyl radical.

Preferably, p represents 0 or 1.

Preferably, $AK_1$ and $AK_2$, which may be identical or different, denote a saturated linear $C_1$-$C_6$ hydrocarbon-based chain.

Preferably, $CAT^+$ represents a cationic radical selected from:
- a 5- to 8-membered cationic heterocyclic radical selected from imidazoliums, piperaziniums, pyrrolidiniums, morpholiniums or piperidiniums optionally substituted with one or more radicals, which may be identical or different, selected from linear or branched $C_1$-$C_4$ alkyl radicals or $C_1$-$C_4$ hydroxyalkyl radicals;
- a tri($C_1$-$C_4$)alkylammonium radical selected from triethylammonium, triethylammonium, dimethylethylammonium, diethylmethylammonium, diisopropylmethylammonium, diethylpropyl-ammonium and dimethyl-beta-hydroxyethylammonium;
- a 5- to 8-membered heterocyclic radical selected from the following radicals: piperidine, pyrrolidine, morpholine, substituted with an alkyl radical substituted with a tri(hydroxy)($C_1$-$C_4$)alkyl-ammonium radical or with a cationic heterocyclic radical, or a pyrrolidinium cationic heterocycle, optionally substituted with one or more radicals, which may be identical or different, selected from linear or branched $C_1$-$C_4$ alkyl radicals or $C_1$-$C_4$ hydroxyalkyl radicals, or a tri(hydroxy)($C_1$-$C_4$)alkylammonium radical.

Even more preferably, $CAT^+$ represents a cationic radical selected from:
- a cationic heterocylic radical selected from imidazoliums, piperaziniums, pyrrolidiniums, morpholiniums or piperidiniums optionally substituted with one or more linear or branched $C_1$-$C_4$ alkyl radicals, which may be identical or different,
- a tri($C_1$-$C_4$)alkylammonium radical selected from trimethyl-ammonium, triethylammonium and dimethyl-beta-hydroxyethylammonium,
- a 5- to 8-membered heterocyclic radical selected from the following radicals: piperidine, pyrrolidine, morpholine, substituted with a radical selected from methyltrimethylammonium, methyl-diethylmethylammonium, methyl (N-methylpyrrolidinium) and trimethylammonium radicals.

According to a first, particularly preferred, variant of the invention, B represents a covalent bond or a carbonyl radical CO, $AK_1$ represents a saturated linear $C_1$-$C_4$ hydrocarbon-based chain, p is equal to 0 and $CAT^+$ is selected from imidazolium, piperazinium, pyrrolidinium, morpholinium or piperidinium radicals, optionally substituted with a $C_1$-$C_2$ alkyl radical; the following radicals: piperidine, pyrrolidine, morpholine substituted with a methyltrimethylammonium, methyldiethylmethylammonium, methyl(N-methylpyrrolidinium) or trimethylammonium radical; and trimethyl-ammonium, triethylammonium or dimethyl-beta-hydroxyethylammonium radicals.

According to a second, particularly preferred, variant of the invention, B represents a covalent bond or a carbonyl radical CO, $AK_1$ represents a saturated linear $C_1$-$C_4$ hydrocarbon-based chain, p is equal to 1, A represents an oxygen atom or an NH radical and $CAT^+$ is selected from imidazolium, piperazinium, pyrrolidinium, morpholinium or piperidinium radicals, optionally substituted with a $C_1$-$C_2$ alkyl radical; the following radicals: piperidine, pyrrolidine, morpholine, piperidine substituted with a methyltrimethylammonium, methyldimethylethylammonium, methyl(N-methylpyrrolidinium) or trimethylammonium radical; and trimethylammonium, triethylammonium or dimethyl-beta-hydroxyethylammonium radicals.

Preferably, $R_2$, $R_3$, $R_4$ and $R_5$, independently of one another, are selected from a hydrogen atom and $C_1$-$C_4$ alkyl radicals. Even more preferably, $R_2$, $R_3$, $R_4$ and $R_5$ are identical and represent a hydrogen atom.

Preferably, $R'_4$, $R'_5$ and $R'_7$ are identical and represent hydrogen atoms.

Preferably, $R_6$ is a hydrogen atom.

The cationic 6-aminoindolines of general formula (I) may be in free form or in the form of salts, such as addition salts with a mineral acid preferably selected from hydrochlorides, hydrobromides, sulphates or phosphates, or with an organic acid, for instance citrates, succinates, tartrates, lactates, tosylates, benzenesulphonates, acetates, para-toluenesulphonates, formates or methanesulphonates.

The cationic 6-aminoindolines of general formula (I) may also be in the form of solvates, for example a hydrate or a solvate of a linear or branched alcohol such as ethanol or isopropanol.

In the context of the invention, the term "derivative of formula (I)" means any mesomeric or isomeric forms.

The electrical neutrality of the compounds of formula (I) is ensured by a cosmetically acceptable organic or mineral anion or a mixture of cosmetically acceptable organic or mineral anions, denoted $An^-$.

An– represents an anion or a mixture of anions selected, for example, from a halide, such as chloride, bromide, fluoride or iodide; a hydroxide; a sulphate; a hydrogen sulphate; an alkyl sulphate for which the linear or branched alkyl part is $C_1$-$C_6$, for instance the methyl sulphate or ethyl sulphate ion; carbonates and hydrogen carbonates; carboxylic acid salts such as formate, acetate, citrate, tartrate or oxalate; alkylsulphonates for which the linear or branched alkyl part is a $C_1$-$C_6$, for instance the methylsulphonate ion; arylsulphonates for which the aryl part, preferably phenyl, is optionally substituted with one or more $C_1$-$C_4$ alkyl radicals, for instance 4-tolylsulphonate; alkylsulphonyls such as mesylate.

Preferably, the cationic 6-aminoindolines of general formula (I) are selected from the following compounds:

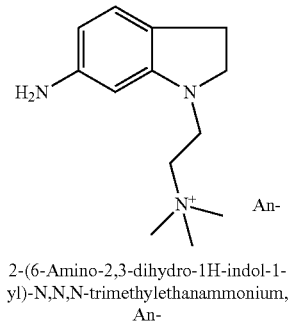

2-(6-Amino-2,3-dihydro-1H-indol-1-yl)-N,N,N-trimethylethanammonium, An- (Compound 1)

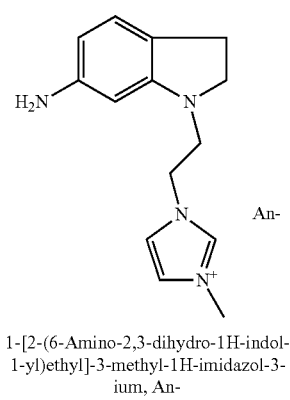

1-[2-(6-Amino-2,3-dihydro-1H-indol-1-yl)ethyl]-3-methyl-1H-imidazol-3-ium, An- (Compound 2)

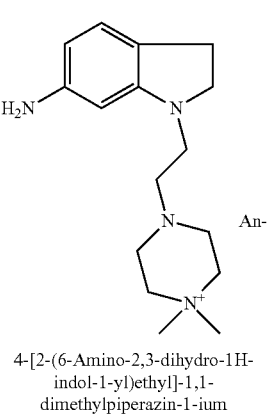

4-[2-(6-Amino-2,3-dihydro-1H-indol-1-yl)ethyl]-1,1-dimethylpiperazin-1-ium (Compound 3)

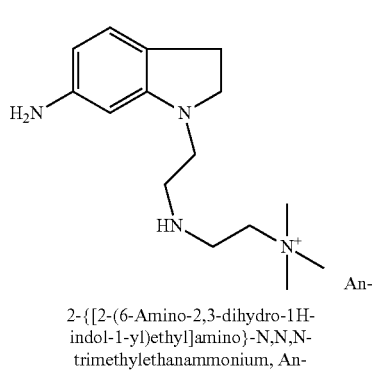

2-{[2-(6-Amino-2,3-dihydro-1H-indol-1-yl)ethyl]amino}-N,N,N-trimethylethanammonium, An- (Compound 4)

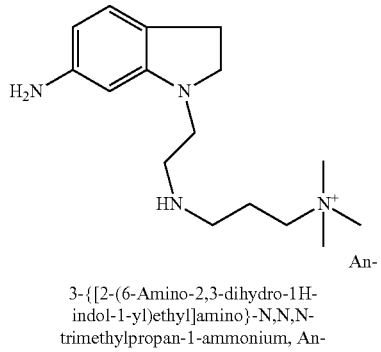

3-{[2-(6-Amino-2,3-dihydro-1H-indol-1-yl)ethyl]amino}-N,N,N-trimethylpropan-1-ammonium, An- (Compound 5)

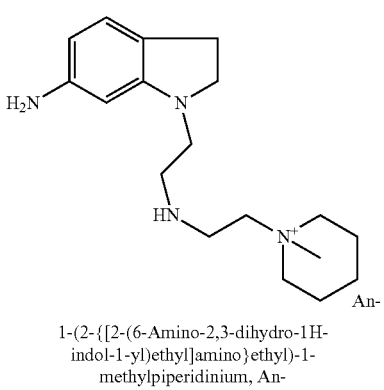

1-(2-{[2-(6-Amino-2,3-dihydro-1H-indol-1-yl)ethyl]amino}ethyl)-1-methylpiperidinium, An- (Compound 6)

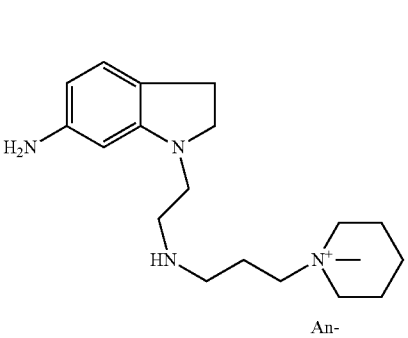

1-(3-{[2-(6-Amino-2,3-dihydro-1H-indol-1-yl)ethyl]amino}propyl)-1-methylpiperidinium, An- (Compound 7)

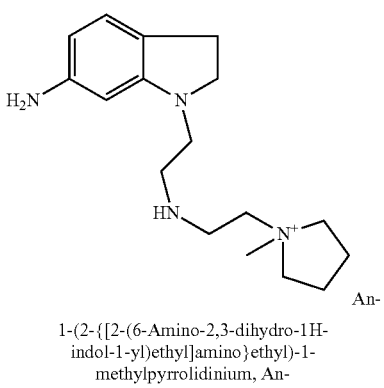

1-(2-{[2-(6-Amino-2,3-dihydro-1H-indol-1-yl)ethyl]amino}ethyl)-1-methylpyrrolidinium, An- (Compound 8)

(Compound 9)

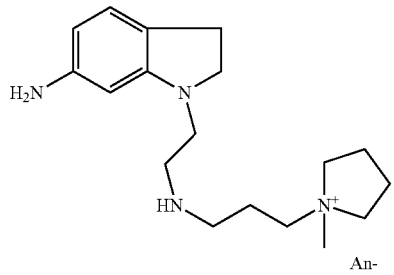

1-(3-{[2-(6-Amino-2,3-dihydro-1H-indol-1-yl)ethyl]amino}propyl)-1-methylpyrrolidinium, An- (Compound 10)

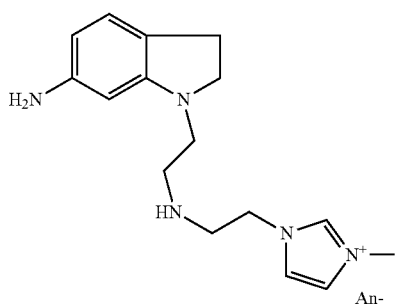

1-(2-{[2-(6-Amino-2,3-dihydro-1H-indol-1-yl)ethyl]amino}ethyl)-3-methyl-1H-imidazol-3-ium, An- (Compound 11)

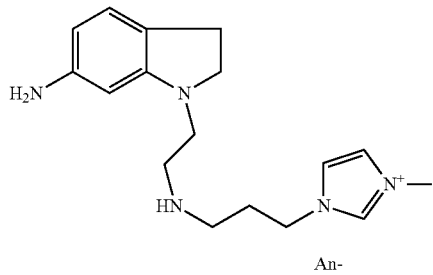

1-(3-{[2-(6-Amino-2,3-dihydro-1H-indol-1-yl)ethyl]amino}propyl)-3-methyl-1H-imidazol-3-ium, An- (Compound 12)

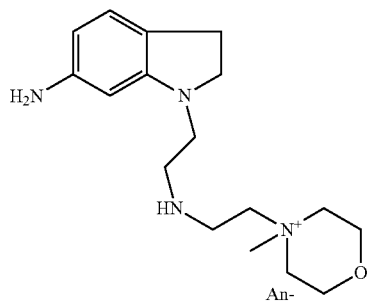

4-(2-{[2-(6-Amino-2,3-dihydro-1H-indol-1-yl)ethyl]amino}ethyl)-4-methylmorpholin-4-ium, An- (Compound 13)

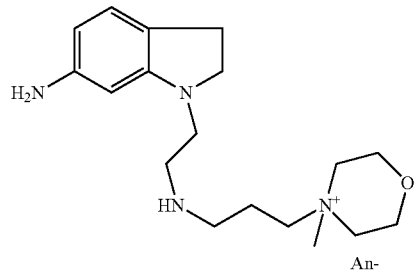

4-(3-{[2-(6-Amino-2,3-dihydro-1H-indol-1-yl)ethyl]amino}propyl)-4-methylmorpholin-4-ium, An- (Compound 14)

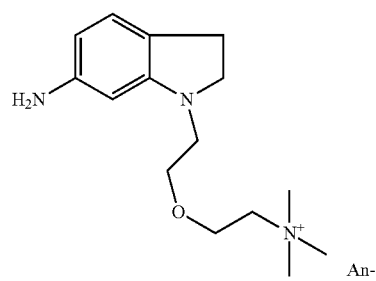

2-[2-(6-Amino-2,3-dihydro-1H-indol-1-yl)ethoxy]-N,N,N-trimethylethanammonium, An- (Compound 15)

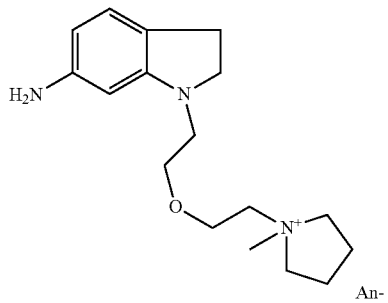

1-{2-[2-(6-Amino-2,3-dihydro-1H-indol-1-yl)ethoxy]-ethyl}-1-methylpyrrolidinium, An- (Compound 16)

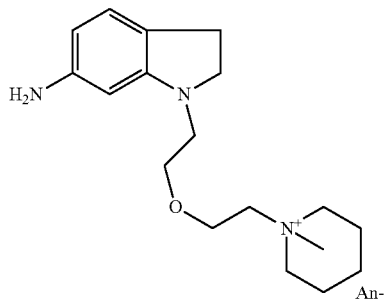

1-{2-[2-(6-Amino-2,3-dihydro-1H-indol-1-yl)ethoxy]ethyl}-1-methylpiperidinium, An- (Compound 17)

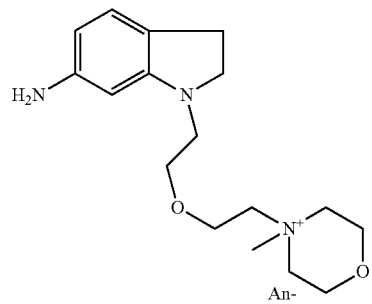

4-{2-[2-(6-Amino-2,3-dihydro-1H-indol-1-yl)ethoxy]ethyl}-4-methylmorpholin-4-ium, An- (Compound 18)

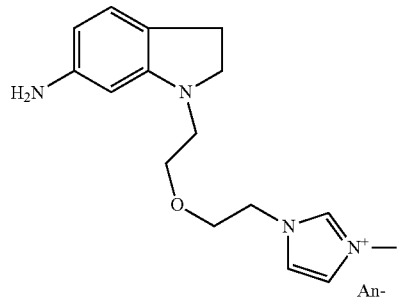

1-{2-[2-(6-Amino-2,3-dihydro-1H-indol-1-yl)ethoxy]ethyl}-3-methyl-1H-imidazol-3-ium, An- (Compound 19)

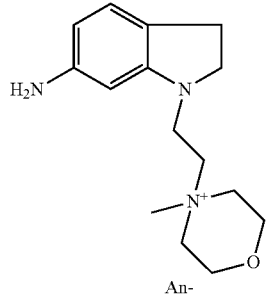

4-[2-(6-Amino-2,3-dihydro-1H-indol-1-yl)ethyl]-4-methylmorpholin-4-ium, An- (Compound 20)

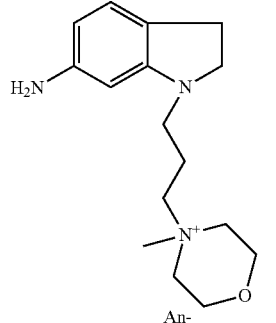

4-[3-(6-Amino-2,3-dihydro-1H-indol-1-yl)propyl]-4-methylmorpholin-4-ium, An- (Compound 21)

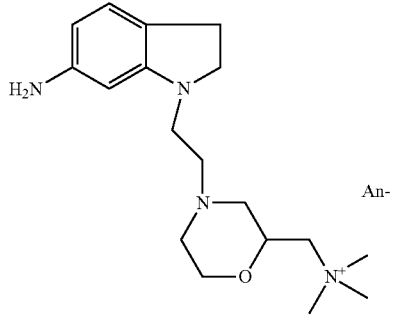

{4-[2-(6-Amino-2,3-dihydro-1H-indol-1-yl)ethyl]morpholin-2-yl}-N,N,N-trimethylmethanammonium, An- (Compound 22)

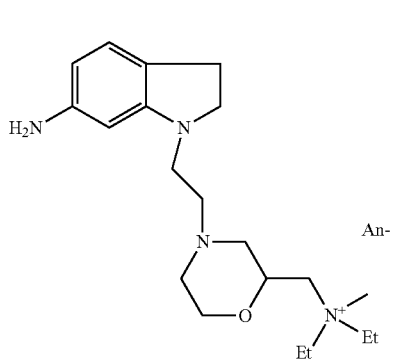

{4-[2-(6-Amino-2,3-dihydro-1H-indol-1-yl)ethyl]morpholin-2-yl}N-methyl-N,N-diethyl-methanammonium, An- (Compound 23)

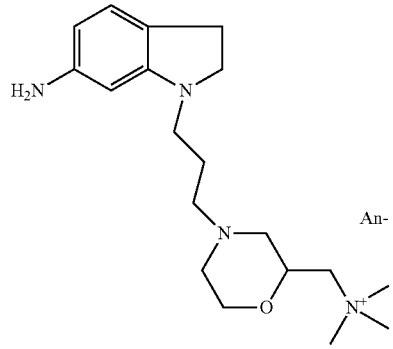

{4-[3-(6-Amino-2,3-dihydro-1H-indol-1-yl)propyl]morpholin-2-yl}-N,N,N-trimethylmethanammonium, An- (Compound 24)

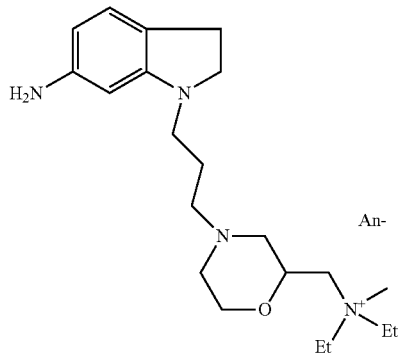

{4-[3-(6-Amino-2,3-dihydro-1H-
indol-1-yl)propyl]morpholin-2-
yl}N-methyl-N,N-diethyl-
methanammonium, An- (Compound 25)

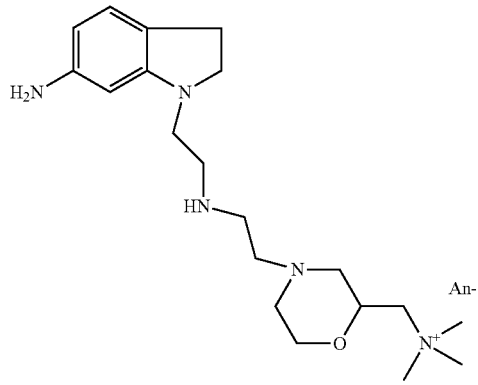

[4-(2-{[2-(6-Amino-2,3-dihydro-1H-
indol-1-yl)ethyl]amino}ethyl)-
morpholin-2-yl]-N,N,N-
trimethylmethanammonium, An- (Compound 26)

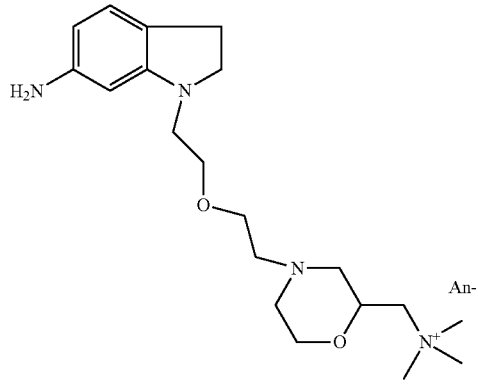

(4-{2-[2-(6-Amino-2,3-dihydro-1H-
indol-1-yl)ethoxy]ethyl}morpholin-
2-yl)-N,N,N-
trimethylmethanammonium, An- (Compound 27)

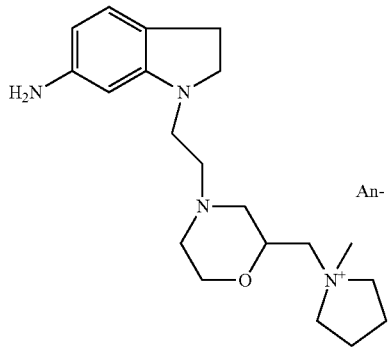

1-({4-[2-(6-Amino-2,3-dihydro-1H-
indol-1-yl)ethyl]morpholin-2-
yl}methyl)-1-methylpyrrolidinium,
An- (Compound 28)

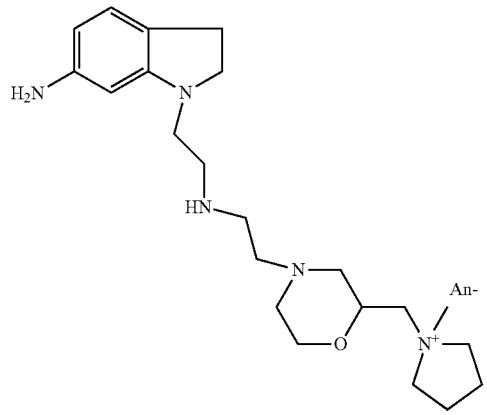

1-{[4-(2-{[2-(6-Amino-2,3-dihydro-
1H-indol-1-yl)ethyl]amino}ethyl)-
morpholin-2-yl]-methyl}-1-
methylpyrrolidinium, An- (Compound 29)

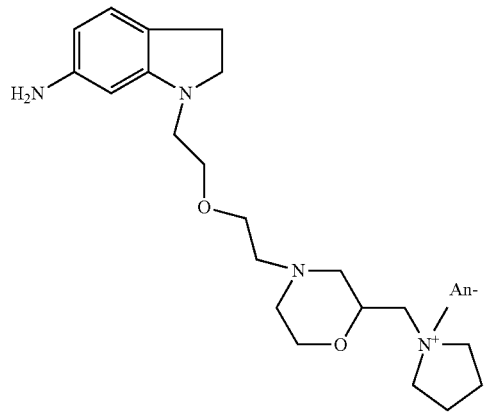

1-[(4-{2-[2-(6-Amino-2,3-dihydro-
1H-indol-1-yl)ethoxy]ethyl}-
morpholin-2-yl)-methyl]-1-
methylpyrrolidinium, An- (Compound 30)

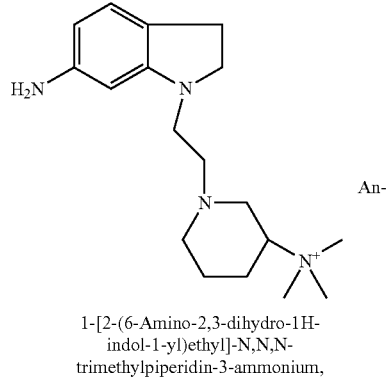

1-[2-(6-Amino-2,3-dihydro-1H-
indol-1-yl)ethyl]-N,N,N-
trimethylpiperidin-3-ammonium,
An- (Compound 31)

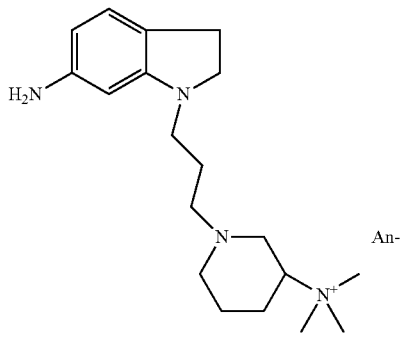

1-[3-(6-Amino-2,3-dihydro-1H-indol-
1-yl)propyl]-N,N,N-
trimethylpiperidin-3-ammonium, An- (Compound 32)

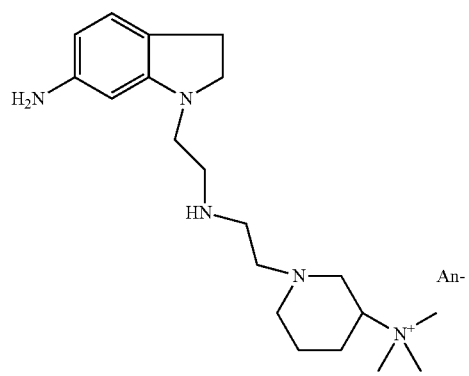

1-(2-{[2-(6-Amino-2,3-dihydro-1H-
indol-1-yl)ethyl]amino}ethyl)-
N,N,N-trimethylpiperidin-3-
ammonium, An- (Compound 33)

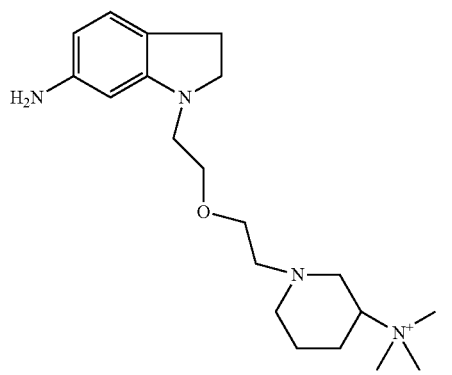

1-{2-[2-(6-Amino-2,3-dihydro-1H-
indol-1-yl)ethoxy]ethyl}-N,N,N-
trimethylpiperidin-3-ammonium, An- (Compound 34)

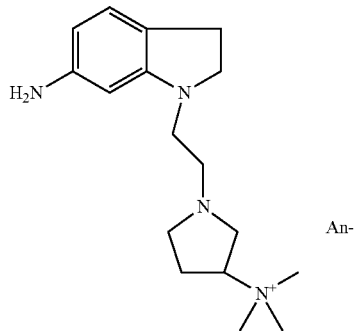

1-[2-(6-Amino-2,3-dihydro-1H-
indol-1-yl)ethyl]-N,N,N-
trimethylpyrrolidin-3-ammonium, An- (Compound 35)

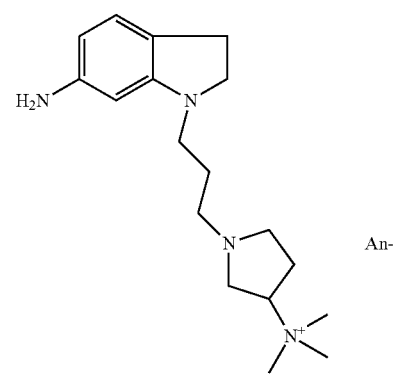

1-[3-(6-Amino-2,3-dihydro-1H-indol-
1-yl)propyl]-N,N,N-
trimethylpyrrolidin-3-ammonium,
An- (Compound 36)

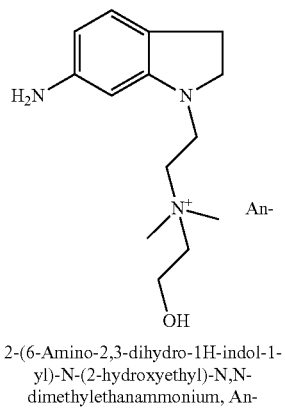

2-(6-Amino-2,3-dihydro-1H-indol-1-yl)-N-(2-hydroxyethyl)-N,N-dimethylethanammonium, An- (Compound 37)

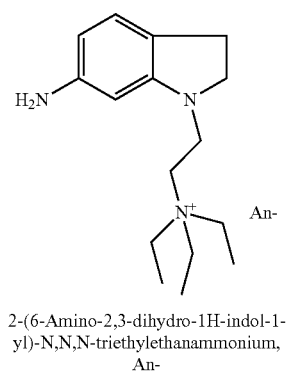

2-(6-Amino-2,3-dihydro-1H-indol-1-yl)-N,N,N-triethylethanammonium, An- (Compound 38)

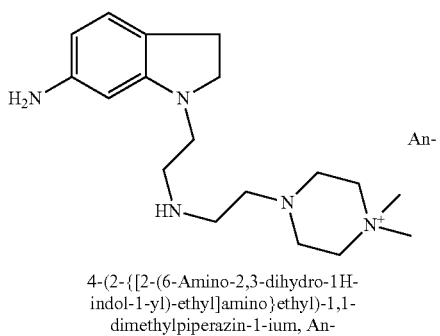

4-(2-{[2-(6-Amino-2,3-dihydro-1H-indol-1-yl)-ethyl]amino}ethyl)-1,1-dimethylpiperazin-1-ium, An- (Compound 39)

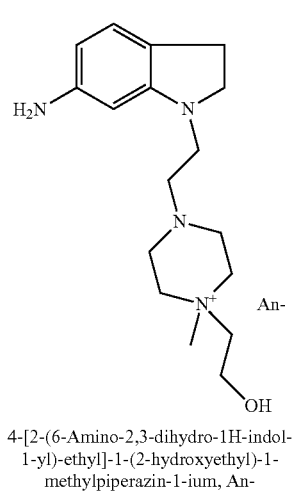

4-[2-(6-Amino-2,3-dihydro-1H-indol-1-yl)-ethyl]-1-(2-hydroxyethyl)-1-methylpiperazin-1-ium, An- (Compound 40)

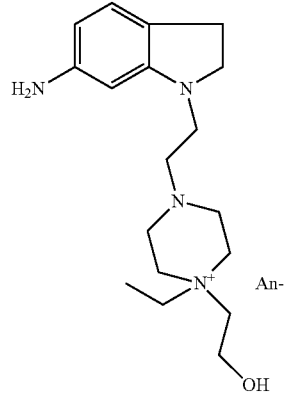

4-[2-(6-Amino-2,3-dihydro-1H-indol-1-yl)-ethyl]-1-ethyl-1-(2-hydroxyethyl)piperazin-1-ium, An- (Compound 41)

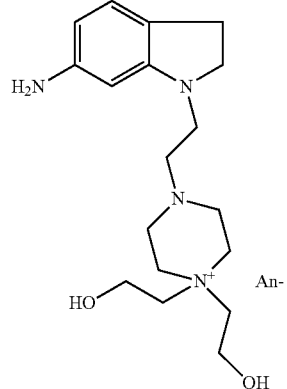

4-[2-(6-Amino-2,3-dihydro-1H-indol-1-yl)-ethyl]-1,1-bis(2-hydroxyethyl)piperazin-1-ium, An- The cationic 6-aminoindolines of general formula (I) according to the present application can be prepared according to various synthesis routes.

The present application also relates to a method for synthesizing a cationic 6-aminoindoline of general formula (I) starting from an indoline of formula (II):

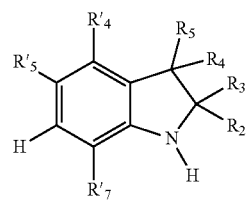

(II)

in which the definitions of the radicals $R_2$, $R_3$, $R_4$, $R_5$, $R'_4$, $R'_5$ an $R'_7$ are those envisaged for the definition of the cationic 6-aminoindoline of general formula (I), said method comprising at least the following steps in this order:
nitration of the indoline of formula (II) so as to obtain a nitroindoline,
substitution of the hydrogen atom borne by the nitrogen atom with the radical —B-AK$_1$-(A-AK$_2$)$_p$-CAT$^+$,
reduction of the nitro group.

When B denotes a covalent bond and p=0, the substitution of the hydrogen atom borne by the nitrogen atom with the radical —B-AK$_1$-(A-AK$_2$)$_p$-CAT$^+$ can be carried out by means of the following steps:
- alkylation of the nitroindoline so as to substitute the nitrogen atom with a halohydroxyalkyl group,
- substitution of the hydroxyl group of the hydroxyalkyl with a sulphonyl group by means of an alkylsulphonyl halide or of an arylsulphonyl halide,
- substitution of the sulphonyl group with an aminoalkoxide or an amine so as to obtain the cationic radical or so as to obtain a precursor of the cationic radical, depending on the nature of the reactant,
- if the substitution carried out in the preceding step results in a precursor of the cationic radical, cationization of the precursor,
- reduction of the nitro group.

This method is summarized in the scheme below:

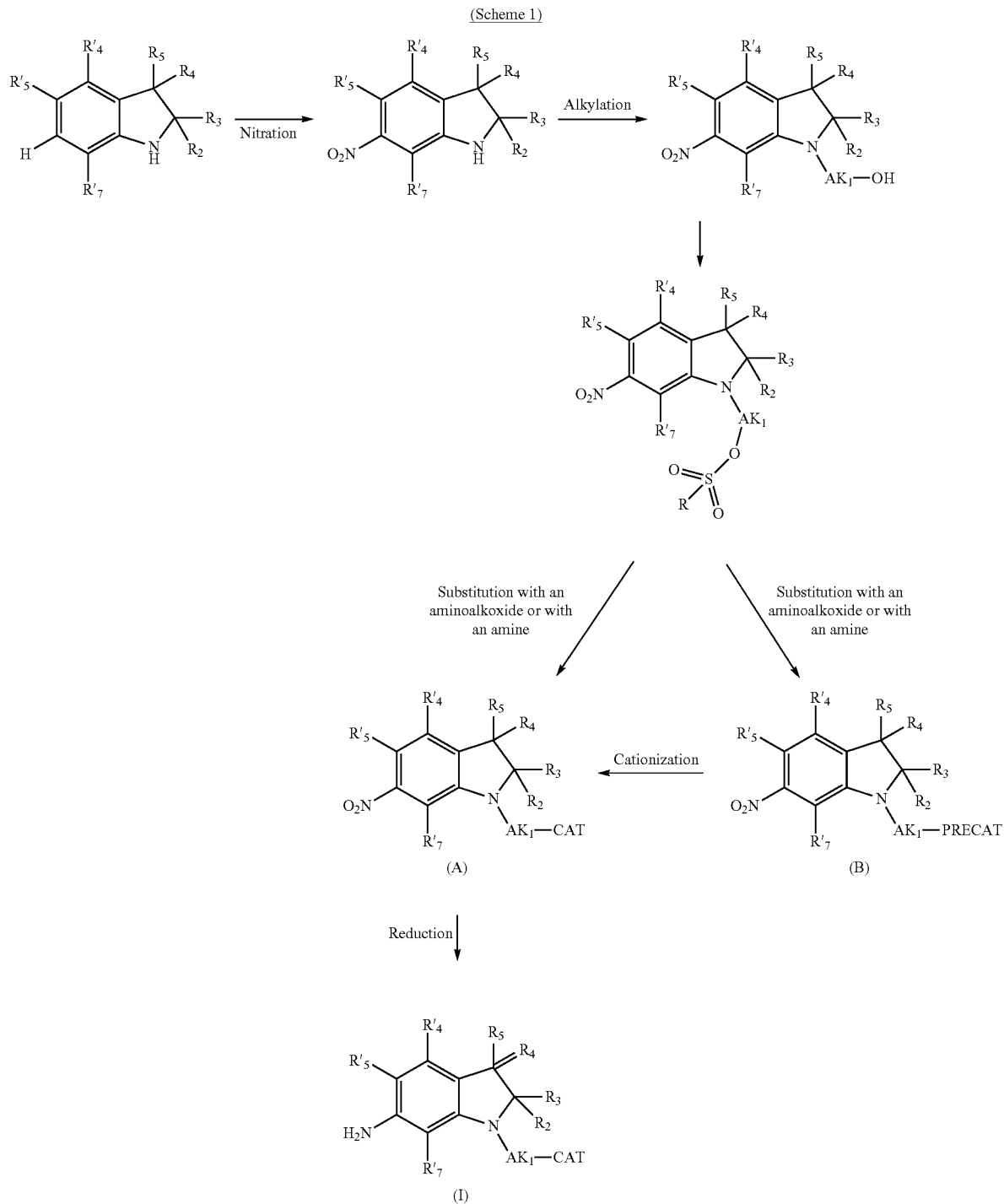

R denote for example a methyl, phenyl, toluoyl group.

When B denotes a covalent bond, and p=0, R denotes a methyl, phenyl or tolyl group, for example.

When B denotes a carbonyl radical and p=0, the substitution of the hydrogen atom borne by the nitrogen atom with the radical —B-AK$_1$-(A-AK$_2$)$_p$-CAT$^+$ can be carried out by means of the following steps:

acylation of the NH group by means of a haloacetyl halide,
then substitution of the halogen with the cationic group CAT or with an aminoalkoxide or an amine so as to obtain a precursor of the cationic group,
cationization of the precursor if the product obtained in the preceding step is not cationic,
reduction of the nitro group.

This method is summarized in the scheme below:

When B denotes a carbonyl radical and p=1 or 2, the substitution of the hydrogen atom borne by the nitrogen atom with the radical —B-AK$_1$-(A-AK$_2$)$_p$-CAT$^+$ can be carried out by means of the following steps:

acylation of the NH group by means of a haloacetyl halide,
substitution of the halogen with a group HA-AK$_2$—X, X being a halogen,
substitution of the halogen with the cationic group CAT or with an aminoalkoxide or an amine so as to obtain a precursor of the cationic group,
cationization of the precursor if the product obtained in the preceding step is not cationic,
reduction of the nitro group.

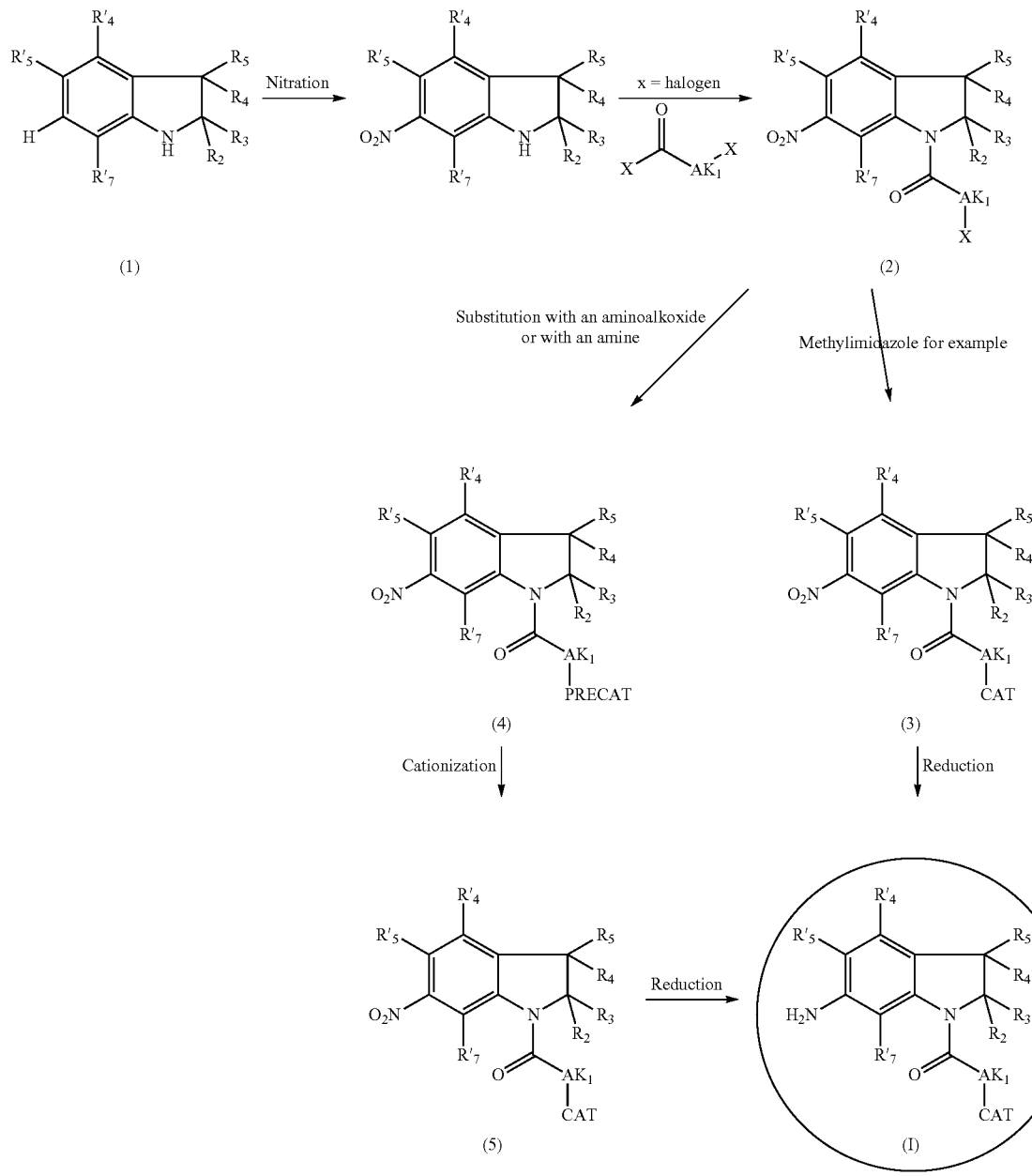

This method is summarized in the scheme below:
(Scheme 3)
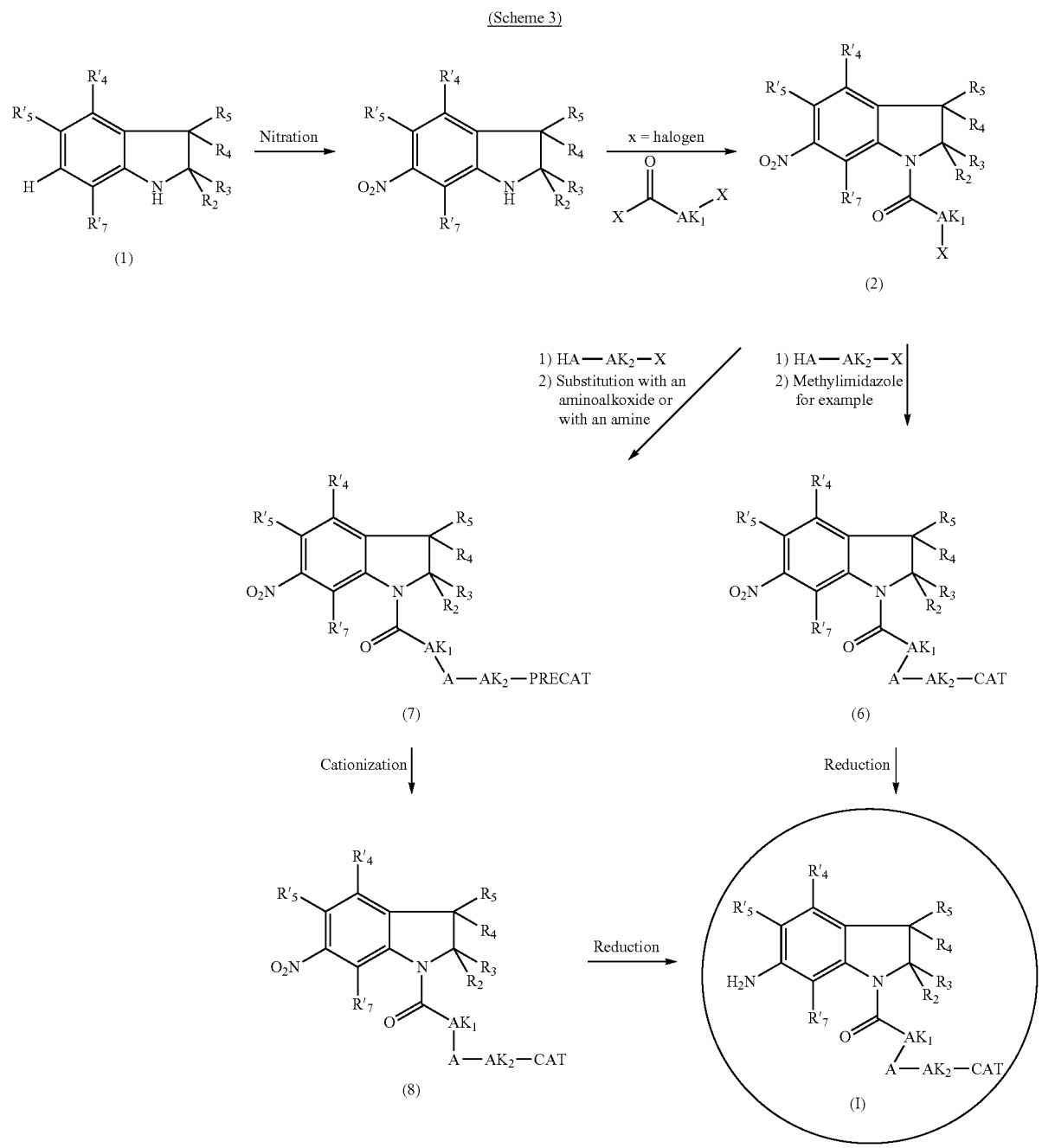
(Scheme 4)
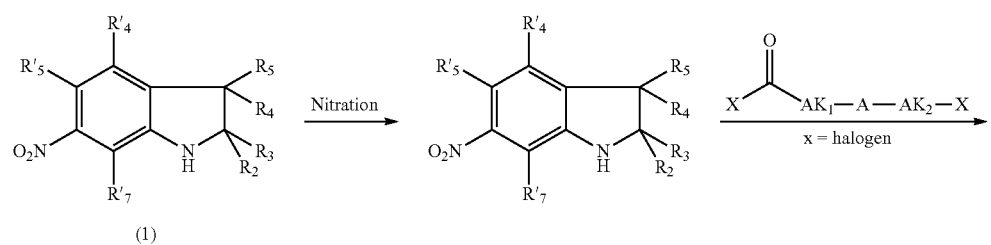

-continued

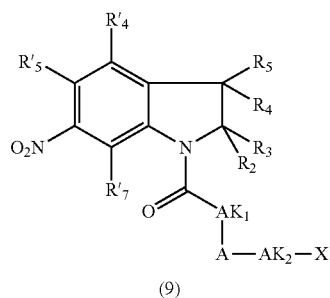

(9)

Substitution with an aminoalkoxide or with an amine ↙    Methylimidazole for example ↓

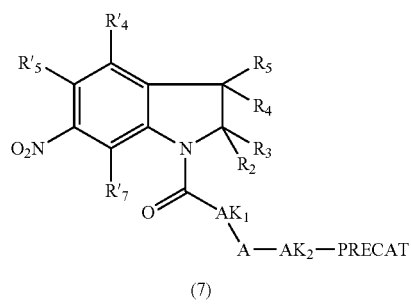

(7)

Cationization ↓

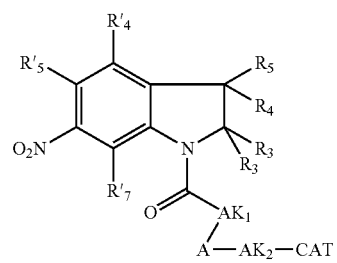

(6)

Reduction ↓

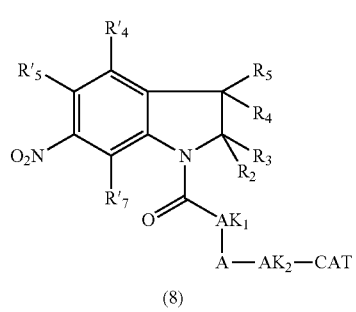

(8)

Reduction →

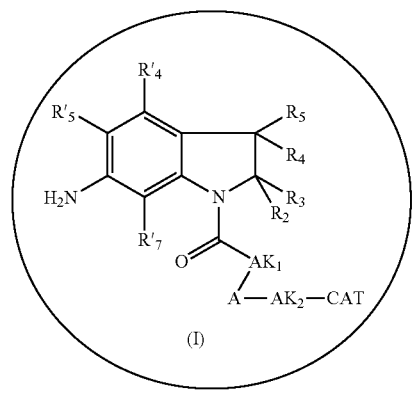

(I)

When B denotes a covalent bond and p=1 or 2, the substitution of the hydrogen atom borne by the nitrogen atom with the radical —B-AK$_1$-(A-AK$_2$)$_p$-CAT$^+$ can be carried out by means of the following steps:
- alkylation of the nitroindoline so as to substitute the nitrogen atom with an alkyl dihalide,
- substitution with a hydroxyalkylamine,
- substitution of the hydroxyl group of the hydroxyalkylamine with a sulphonyl group by means of an alkylsulphonyl halide or an arylsulphonyl halide,
- substitution of the sulphonyl group with an aminoalkoxide or an amine so as to obtain the cationic radical or so as to obtain a precursor of the cationic radical, depending on the nature of the reactant,
- if the substitution carried out in the preceding step results in a precursor of the cationic radical, cationization of the precursor,
- reduction of the nitro group.

This method is summarized in the scheme below:
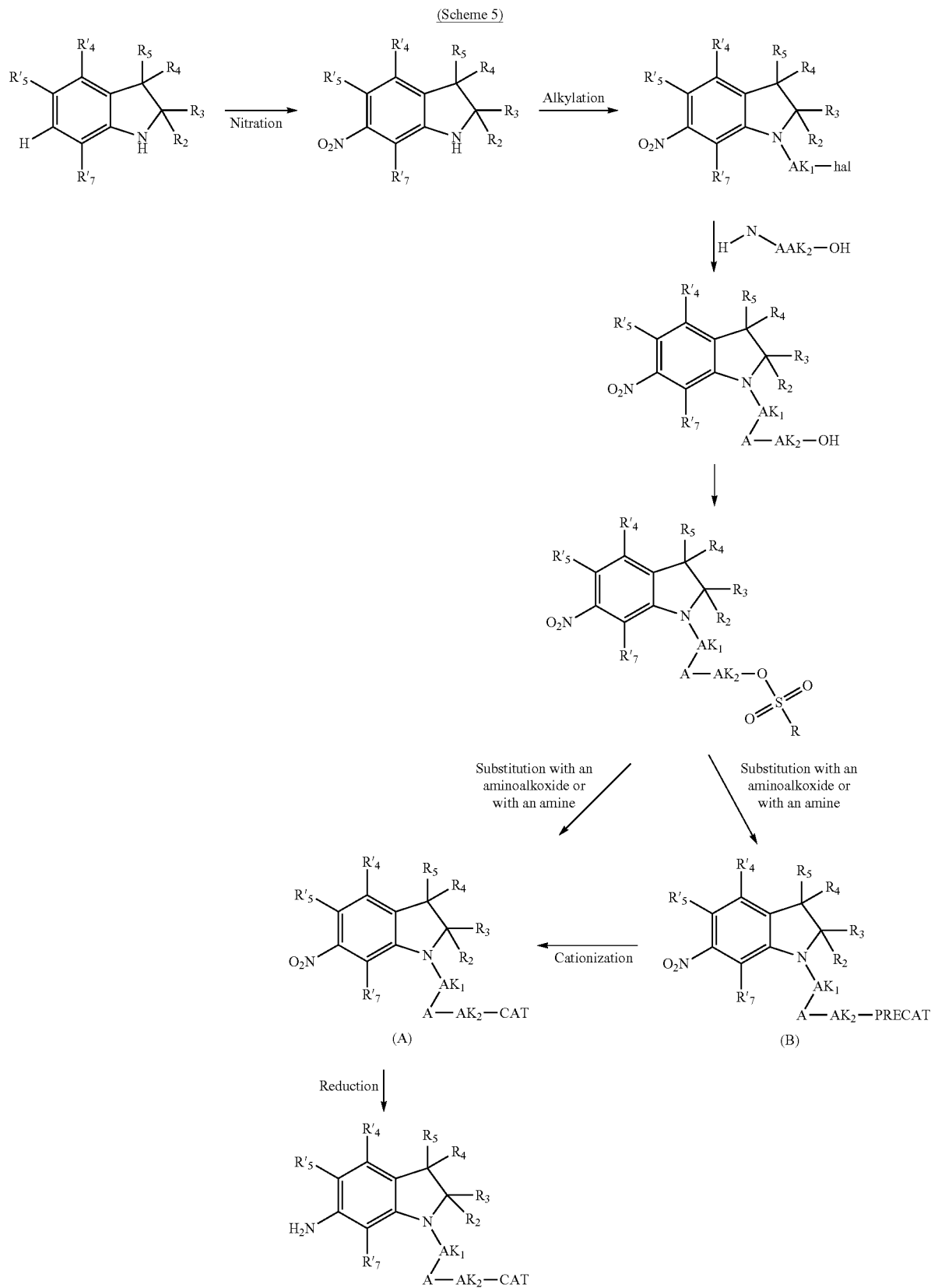
(Scheme 5)

With $AK_1$, $AK_2$ and A having the same meanings as in formula (I).

CAT=cationic radical as defined previously, the electrical neutrality being ensured by $An^-$ as defined previously.

PRECAT=radical that is cationizable into a cationic radical CAT.

R denotes a methyl, phenyl or tolyl group, for example.

The nitration of the indo line is carried out, for example, in a sulphuric acid/nitric acid mixture at a temperature below 15° C. for 15 min to 20 hours.

In Scheme 1, the alkylation reaction is carried out in a dipolar solvent such as acetonitrile, THF or in an alcohol such as ethanol, for example, in the presence of a base such as triethylamine, ethyldiisopropylamine, sodium hydroxide or potassium hydroxide, for example, with 1 to 2 equivalents of hydroxyalkyl halide for 1 to 24 hours at a temperature from 20° C. to the reflux temperature of the solvent.

The hydroxyl function thus introduced is then substituted with a halide (for example mesyl or tosyl halide) in a solvent such as acetonitrile, THF or in an alcohol such as ethanol, for example, in the presence of a base such as triethylamine, ethyldiisopropylamine, sodium hydroxide or potassium hydroxide, for example, for 1 to 24 hours at a temperature ranging from 20° C. to the reflux temperature of the solvent.

The substitution of the leaving group introduced in the preceding step is carried out either by reaction with an aromatic tertiary amine such as methylimidazole, to give the compounds (A), or by reaction with a particular primary or secondary amine, for instance N,N-dimethylethylenediamine or 2-piperidin-1-ylethanamine to give the compounds (B). Alkylation of the compounds (B) with at least one equivalent of alkyl halide or methyl sulphate in a solvent such as THF, acetonitrile, dioxane or ethyl acetate for 15 min to 24 h at a temperature ranging from 15° C. to the reflux temperature of the solvent gives the compounds (A).

The reduction of the nitro group of the compounds (A) is carried out under conventional conditions, for example by performing a hydrogenation reaction under heterogeneous catalysis in the presence of Pd/C, Pd(II)/C, Ni/Ra, etc., or alternatively by performing a reduction reaction with a metal, for example with zinc, iron, tin, etc. (see Advanced Organic Chemistry, 3rd Edition, J. March, 1985, Wiley Interscience and Reduction in organic Chemistry, M. Hudlicky, 1983, Ellis Horwood Series Chemical Science). This technique is applied to the reduction steps of Schemes 2, 3, 4 and 5.

In Schemes 2, 3 and 4, the acylation step is carried out under conventional conditions for example by reaction with a haloacetyl halide in a polar solvent of alcohol, alkyl acetate, THF, dioxane, etc., type at a temperature between 0° C. and 100° C. According to the nature of the haloacetyl, the compounds (2) or (9) are obtained.

According to the nature of the amine subsequently used, the nitrogenous compounds (3) or (6) are directly obtained, or it is necessary to substitute the halogen of the compound (2) with an amine or an aminoalkoxide to give the derivatives (4) or (7) which are subsequently cationized with an alkyl halide, an alkyl sulphate or an alkyl carbonate in a solvent of $CH_3CN$, $CHCl_3$, THF, dioxane, ethyl acetate or acetone type, to give the nitrogenous precursors (5) or (8).

In Scheme 5, the alkylation step is carried out under conventional conditions, for example, by reaction with an alkyl dihalide, for instance 1,2-ethylene dihalide, in a polar solvent such as alcohol, alkyl acetate, THF, dioxane, DMF, etc., at a temperature between 0° C. and 150° C. in the presence of an organic or mineral base, to give the desired compound. The resulting compound is then substituted with an amine of alkylhydroxy type, for instance 2-aminoethanol. This step is continued by means of a reaction for protection of the alcohol with an $SO_3R$ group of methanesulphonic, benzenesulphonic or methylbenzenesulphonic type, so as to obtain a leaving group of $SO_3R$ type which can be easily displaced with an amine or an amino alkoxide corresponding to (A) or (B).

The present application also relates to the uses of a cationic 6-aminoindoline of general formula (I) as a coupler for the dyeing of keratin fibres, in particular human keratin fibres such as the hair.

The present application also relates to a cosmetic dyeing composition in particular for keratin fibres such as the hair, comprising, in a medium suitable for dyeing, at least one cationic 6-aminoindoline of general formula (I).

Preferably, the concentration of the cationic 6-aminoindoline of general formula (I) is between 0.0001% and 20%, preferably between 0.005% and 6% by weight, relative to the total weight of the composition.

The medium suitable for dyeing generally comprises water or a mixture of water and at least one organic solvent such as, for example, linear or branched $C_1$-$C_4$ lower alcohols, such as ethanol and isopropanol; polyols and polyol ethers, for instance 2-butoxyethanol, propylene glycol, propylene glycol monomethyl ether, diethylene glycol monomethyl ether and monoethyl ether, glycerol and also aromatic alcohols, for instance benzyl alcohol or phenoxyethanol, and mixtures thereof.

Advantageously the cosmetic composition comprises at least one cosmetic adjuvant selected from the group consisting of antioxidants, penetrants, sequestrants, fragrances, buffers, dispersants, surfactants, conditioning agents, film formers, polymers, ceramides, preservatives, pearlizing or opacifying agents, vitamins or provitamins.

The above adjuvants are generally present in an amount, for each of them, of between 0.01% and 20% by weight, relative to the weight of the composition.

The composition also comprises at least one oxidation base. These bases may in particular be selected from para-phenylenediamines, bis-phenylalkylenediamines, para-aminophenols, ortho-aminophenols and heterocyclic bases, and their addition salts.

Among the para-phenylenediamines, examples that may be mentioned more particularly include para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methyl-aniline, N,N-bis(β-hydroxyethyl)-para-phenylenediamine, 4-N,N-bis(β-hydroxyethyl)amino-2-methylaniline, 4-N,N-bis(β-hydroxy-ethyl)amino-2-chloro aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl,β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, 6-(4-aminophenylamino)-hexan-1-ol, N-(4-amino-3-methylphenyl)-N-[3-(1H-imidazol-1-yl)-propyl]amine and N-(4- aminophenyl)-N-[3-(1H-imidazol-1-yl)propyl]-amine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine and 2-[{2-[(4-aminophenyl)amino]ethyl}(2-hydroxyethyl)amino]ethanol, and the addition salts thereof with an acid, are particularly preferred.

Among the bis(phenyl)alkylenediamines, examples that may be mentioned include N,N'-bis(β-hydroxyethyl)-N,N'-bis(4'-amino-phenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-amino-phenyl)tetramethylenediamine, N,N'-bis(4-methylaminophenyl)tetra-methylenediamine, N,N'-bis(ethyl)-N,N'-bis(4'-amino-3'-methyl-phenyl)ethylenediamine and 1,8-bis(2,5-diaminophenoxy)-3,6-dioxa-octane, and the addition salts thereof with an acid.

Among the para-aminophenols, examples that may be mentioned include para-aminophenol, 4-amino-3-methylphenol, 4-amino-3-fluorophenol, 4-amino-2-chlorophenol, 4-amino-3-chloro-phenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylamino-methyl)phenol, 4-amino-2-fluorophenol, 4-amino-2,6-dichlorophenol, 4-amino-6[((5'-amino-2'-hydroxy-3'-methyl)phenyl)methyl]-2-methylphenol and bis[(5'-amino-2'-hydroxy)phenylmethane, and the addition salts thereof with an acid.

Among the ortho-aminophenols, examples that may be mentioned include 2-aminophenol, 2-amino-5-methylphenol, 2-amino-6-methylphenol and 5-acetamido-2-aminophenol, and the addition salts thereof with an acid.

Among the heterocyclic bases, examples that may be mentioned include pyridine derivatives, pyrimidine derivatives and pyrazole derivatives.

Among the pyridine derivatives, mention may be made of the compounds described, for example, in patents GB 1 026 978 and GB 1 153 196, for instance 2,5-diaminopyridine, 2-(4-methoxy-phenyl)amino-3-aminopyridine and 3,4-diaminopyridine, and the addition salts thereof with an acid.

Other pyridine oxidation bases that are useful in the present invention are the 3-aminopyrazolo[1,5-a]pyridine oxidation bases or the addition salts thereof described, for example, in patent application FR 2 801 308. Examples that may be mentioned include pyrazolo[1,5-a]pyridin-3-ylamine; 2-acetylaminopyrazolo[1,5-a]-pyridin-3-ylamine; 2-morpholin-4-ylpyrazolo[1,5-a]pyridin-3-ylamine; 3-aminopyrazolo[1,5-a]pyridine-2-carboxylic acid; 2-methoxy-pyrazolo[1,5-a]pyridin-3-ylamine; (3-aminopyrazolo[1,5-a]pyridine-7-yl)methanol; 2-(3-aminopyrazolo[1,5-a]pyridine-5-yl)ethanol; 2-(3-aminopyrazolo[1,5-a]pyridin-7-yl)ethanol; (3-aminopyrazolo[1,5-a]-pyridin-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyridin-3-ylamine; pyrazolo-[1,5-a]pyridine-3,5-diamine; 5-morpholin-4-ylpyrazolo[1,5-a]pyridin-3-ylamine; 2-[(3-aminopyrazolo[1,5-a]pyridin-5-yl)-(2-hydroxyethyl)-amino]ethanol; 2-[(3-aminopyrazolo[1,5-a]pyridin-7-yl)-(2-hydroxy-ethyl)amino]ethanol; 3-aminopyrazolo[1,5-a]pyridin-5-ol; 3-amino-pyrazolo[1,5-a]pyridin-4-ol; 3-aminopyrazolo[1,5-a]pyridin-6-ol; 3-aminopyrazolo[1,5-a]pyridine-7-ol; and the addition salts thereof with an acid.

Among the pyridine bases that are of use in the present invention, mention may also be made of the compounds described in patent applications EP 1792903 and EP 1792606 and the addition salts thereof.

Among the pyrimidine derivatives, mention may be made of the compounds described, for example, in patents DE 2 359 399; JP 88-169571; JP 05-63124; EP 0770375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof and the tautomers thereof, when a tautomeric equilibrium exists.

Among the pyrazolopyrimidine derivatives, mention may be made of the compounds described, for example, in patent applications EP 0847271, EP 0926149 and EP 1147109 and the addition salts thereof.

Among the pyrazole derivatives that may be mentioned are the compounds described in patents DE 3 843 892, DE 4 133 957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)-pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-amino ethyl)amino-1,3-dimethylpyrazole, 3,4,5-triamino-pyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof.

As oxygen bases, mention may also be made of the derivatives of diamino-N,N-dihydropyrazolone of formula (IV) or an addition salt or solvate thereof:

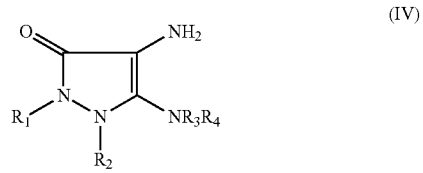

(IV)

in which:

R₁, R₂, R₃ and R₄, which may be identical or different, represent:
  a linear or branched $C_1$-$C_6$ alkyl radical optionally substituted with one or more radicals selected from the group consisting of an OR₅ radical, an NR₆R₇ radical, a carboxyl radical, a sulphonic radical, a carboxamido radical CONR₆R₇, a sulphonamido radical SO₂NR₆R₇, a heteroaryl, an aryl optionally substituted with a ($C_1$-$C_4$) alkyl group, a hydroxyl, a $C_1$-$C_2$ alkoxy, an amino, or a (di)($C_1$-$C_2$)alkylamino;

an aryl radical optionally substituted with one or more $(C_1-C_4)$alkyl, hydroxyl, $C_1-C_2$ alkoxy, amino or (di)$(C_1-C_2)$alkylamino;

a 5- or 6-membered heteroaryl radical, optionally substituted with one or more radicals selected from $(C_1-C_4)$ alkyl and $(C_1-C_2)$alkoxy;

$R_3$ and $R_4$ can also represent a hydrogen atom;

$R_5$, $R_6$ and $R_7$, which may be identical or different, represent a hydrogen atom; a linear or branched $C_1-C_4$ alkyl radical optionally substituted with one or more radicals selected from the group consisting of a hydroxyl, a $C_1-C_2$ alkoxy, a carboxamido $CONR_8R_9$, a sulphonyl $SO_2R_8$, an aryl optionally substituted with a $(C_1-C_4)$alkyl, a hydroxyl, a $C_1-C_2$ alkoxy, an amino or a (di)$(C_1-C_2)$alkylamino; an aryl optionally substituted with a $(C_1-C_4)$alkyl, a hydroxyl, a $C_1-C_2$ alkoxy, an amino or a (di)$(C_1-C_2)$alkylamino;

$R_6$ and $R_7$, which may be identical or different, can also represent a carboxamido radical $CONR_8R_9$; a sulphonyl $SO_2R_8$;

$R_8$ and $R_9$, which may be identical or different, represent a hydrogen atom; a linear or branched $C_1-C_4$ alkyl radical optionally substituted with one or more hydroxyl or $C_1-C_2$ alkoxy;

$R_1$ and $R_2$, on the one hand, and $R_3$ and $R_4$, on the other hand, can form, with the nitrogen atoms to which they are attached, a saturated or unsaturated heterocycle which comprises 5 to 7 ring members and which is optionally substituted with one or more radicals selected from the group consisting of halogen atoms, amino, (di)$(C_1-C_4)$alkylamino, hydroxyl, carboxyl, carboxamido and $(C_1-C_2)$alkoxy radicals, and $C_1-C_4$ alkyl radicals optionally substituted with one or more hydroxyl, amino, (di)alkylamino, alkoxy, carboxyl or sulphonyl radicals;

$R_3$ and $R_4$ can also form, together with the nitrogen atom to which they are attached, a 5- or 7-membered heterocycle, the carbon atoms of which can be replaced with an optionally substituted oxygen or nitrogen atom.

These derivatives of diamino-N,N-dihydropyrazolone are in particular described in application FR 2866338; a particularly preferred derivative is 2,3-diamino-6,7-dihydro-1H,5H-pyrazolo[1,2-a]pyrazol-1-one dimethanesulphonate.

As oxidation bases, mention may also be made of the derivatives of diamino-N,N-dihydropyrazolone of formula (I) or an addition salt or solvate thereof:

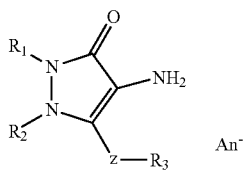

in which:
Z represents independently:
a single covalent bond,
a divalent radical selected from
an oxygen atom,
an —$NR_6$ radical, with $R_6$ representing a hydrogen atom or a $C_1-C_6$ alkyl radical, or $R_6$, with $R_3$, form, together with the nitrogen atom to which they are attached, a substituted or unsubstituted, saturated or unsaturated, aromatic or nonaromatic, 5- to 8-membered heterocycle, optionally containing one or more other heteroatoms or groups selected from N, O, S, $SO_2$ and —CO—, it being possible for the heterocycle to be cationic and/or substituted with a cationic radical, an —N+$R_7R_8$— radical with $R_7$ and $R_8$ independently representing an alkyl radical; the alkyl radical may be substituted with an OH or an —Oalkyl, $R_3$ represents:
a hydrogen,
a $C_1-C_{10}$ alkyl radical, which is optionally substituted, it being possible for the alkyl radical to be interrupted with a heteroatom or a group selected from O, N, Si, S, SO and $SO_2$,
a $C_1-C_{10}$ alkyl radical substituted and/or interrupted with a cationic radical,
a halogen,
an $SO_3H$ radical,
a substituted or unsubstituted, saturated, unsaturated or aromatic, 5- to 8-membered ring, optionally containing one or more heteroatoms or groups selected from N, O, S, $SO_2$ and —CO—, it being possible for the ring to be cationic and/or substituted with a cationic radical, $R_1$ and $R_2$, which may be identical or different, represent:
a linear or branched $C_1-C_6$ alkyl radical optionally substituted with one or more radicals selected from an $OR_5$ radical, an $NR_9R_{10}$ radical, a carboxyl radical, a sulphonic radical, a carboxamido radical $CONR_9R_{10}$, a sulphonamido radical $SO_2NR_9R_{10}$, a heteroaryl, an aryl optionally substituted with a $(C_1-C_4)$alkyl, hydroxyl, $C_1-C_2$ alkoxy, amino or (di)$(C_1-C_2)$alkylamino group;
an aryl radical optionally substituted with one or more $(C_1-C_4)$alkyl, hydroxyl, $C_1-C_2$ alkoxy, amino or (di)$(C_1-C_2)$alkylamino;
a 5- or 6-membered heteroaryl radical, optionally substituted with one or more radicals selected from $(C_1-C_4)$ alkyl monosubstituted or polysubstituted with an OH or an —Oalkyl or $(C_1-C_2)$alkoxy;

$R_1$ and $R_2$ can form, with the nitrogen atoms to which they are attached, a saturated or unsaturated heterocycle which comprises 5 to 7 ring members and which is optionally substituted with one or more radicals selected from the group consisting of halogen atoms, amino, (di)$(C_1-C_4)$alkylamino, hydroxyl, carboxyl, carboxamido and $(C_1-C_2)$alkoxy radicals, and $C_1-C_4$ alkyl radicals optionally substituted with one or more hydroxyl, amino, (di)alkylamino, alkoxy, carboxyl or sulphonyl radicals, An– represents an anion or a group of anions making it possible to ensure the electrical neutrality of the compounds of formula (I), on the condition that at least one of the groups Z and $R_3$ represents a cationic radical.

These derivatives of diamino-N,N-dihydropyrazolone are described in patent application FR 2 927 078.

Generally, the concentration of the oxidation base or bases is between 0.0001% and 20%, preferably between 0.005% and 6% by weight, relative to the total weight of the composition.

The composition according to the invention preferably contains at least one additional oxidation coupler other than the cationic 6-aminoindolines of general formula (I).

These oxidation couplers include in particular meta-phenylenediamines, meta-aminophenols, meta-diphenols, naphthalenic couplers and heterocyclic couplers, and the addition salts thereof.

Examples include 2-methyl-5-aminophenol, 5-N-(β-hydroxyethyl)amino-2-methylphenol, 6-chloro-2-methyl-5-aminophenol, 3-aminophenol, 1,3-dihydroxybenzene (or resorcinol), 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis-(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene and the addition salts thereof.

In general the concentration of the oxidation coupler or couplers is between 0.0001% and 20%, preferably between 0.005% and 6% by weight, relative to the total weight of the composition.

Generally speaking, the addition salts with an acid that can be used for the oxidation bases and the couplers are selected in particular from hydrochlorides, hydrobromides, sulphates, citrates, succinates, tartrates, lactates, tosylates, benzenesulphonates, phosphates and acetates.

The dyeing composition in accordance with the invention may further comprise one or more direct dyes, which may in particular be selected from neutral, acidic or cationic nitrobenzene dyes, neutral, acidic or cationic azo direct dyes, neutral, acidic or cationic quinone, and especially anthraquinone, direct dyes, azine direct dyes, methine, azomethine, triarylmethane and indoamine direct dyes and natural direct dyes. The composition according to the invention preferably comprises at least one dye selected from cationic direct dyes and natural direct dyes.

Among the cationic direct dyes that can be used according to the invention, mention may be made of the cationic azo direct dyes described in patent applications WO 95/15144, WO 95/01772 and EP-714954.

These compounds include especially the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]pyridinium methylsulphate.

The direct natural dyes which can be used according to the invention include lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes and in particular henna-based poultices or extracts, may also be used.

The direct dye or dyes represents or represent, preferably, from 0.001% to 20% by weight, approximately, of the total weight of the composition, and even more preferably approximately from 0.005% to 10% by weight.

The person skilled in the art would of course ensure that the adjuvant or adjuvants, additional oxidation dye precursors and direct dyes are selected such that the advantageous properties intrinsically attached to the oxidation dyeing composition in accordance with the invention are not, or not substantially, adversely affected by the intended addition or additions.

The pH of the dyeing composition in accordance with the invention is generally between approximately 3 and 12, and preferably between approximately 5 and 11. It may be adjusted to the desired value by means of acidifying or alkalifying agents which are typically used in the dyeing of keratin fibres or else using conventional buffer systems.

The acidifying agents include, for example, mineral or organic acids other than dicarboxylic acids, for instance hydrochloric acid, orthophosphoric acid, sulphuric acid, carboxylic acids such as acetic acid, tartaric acid, citric acid and lactic acid, and sulphonic acids.

The alkalifying agents include, for example, ammonia, alkali metal carbonates, alkanolamines such as mono-, di- and triethanolamines and their derivatives, sodium hydroxide or potassium hydroxide, and the compounds of formula:

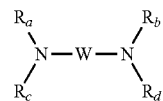

in which W is a propylene residue optionally substituted with a hydroxyl group or a $C_1$-$C_4$ alkyl radical; $R_a$, $R_b$, $R_c$ and $R_d$, which may be identical or different, represent a hydrogen atom or a $C_1$-$C_4$ alkyl or $C_1$-$C_4$ hydroxyalkyl radical.

The cosmetic composition according to the invention may be present in a variety of forms, such as in the form of liquids, creams, gels, or any other form which is appropriate for carrying out dyeing of keratin fibres, and in particular of human hair.

The present application relates to a method in which the composition according to the present invention as defined previously is applied to keratin fibres for a time sufficient for the desired colouration to develop in the presence of an oxidizing agent, the oxidizing agent being applied before, simultaneously with or after the composition.

The colour may be revealed at acidic, neutral or alkaline pH and the oxidizing agent may be added to the composition of the invention just at the time of use or it may be used starting from an oxidizing composition containing it, which is applied simultaneously with or sequentially to the composition of the invention.

In one particular embodiment the composition according to the present invention is mixed, preferably at the time of use, into a composition containing, in a medium appropriate for dyeing, at least one oxidizing agent, this oxidizing agent being present in an amount sufficient to develop a coloration.

In this particular embodiment, a ready-to-use composition is available which is a mixture of a composition according to the invention with at least one oxidizing agent. The resulting mixture is subsequently applied to the keratin fibres for a time sufficient for the desired coloration to develop. After a leave-on time of approximately 3 to 50 minutes, preferably approximately 5 to 30 minutes, the keratin fibres are rinsed, washed with shampoo, rinsed again and then dried.

The oxidizing agents conventionally used for the oxidation dyeing of keratin fibres are, for example, hydrogen peroxide, urea peroxide, alkali metal bromates, persalts such as perborates and persulphates, peracids and oxidase enzymes, including peroxidases, 2-electron oxidoreductases, such as uricases, and 4-electron oxygenases, such as laccases. Hydrogen peroxide is particularly preferred.

The oxidizing composition may further comprise various adjuvants which are used conventionally in compositions for dyeing hair, and are as defined above.

The pH of the oxidizing composition containing the oxidizing agent is such that, after mixing with the dyeing composition, the pH of the resulting composition applied to the keratin fibres preferably ranges between approximately 3 and 12, and even more preferably between 5 and 11. It may be adjusted to the desired value by means of acidifying or alkalifying agents which are typically used in the dyeing of keratin fibres and are as defined above.

The ready-to-use composition which is ultimately applied to the keratin fibres may be present in a variety of forms, such as in the form of liquids, creams or gels or any other form appropriate for carrying out dyeing of keratin fibres, and in particular of human hair.

The present application further provides a method of dyeing keratin fibres, in which the ready-to-use composition is applied to said fibres for a time sufficient to develop the desired coloration.

The time sufficient for the desired coloration to develop corresponds in general to a leave-on time of approximately 3 to 50 minutes, preferably approximately 5 to 30 minutes.

The invention further provides a multi-compartment dyeing device or "kit" in which a first compartment contains the dyeing composition defined above and a second compartment contains an oxidizing composition. This device may be equipped with a means allowing the desired mixture to be delivered to the hair, such as the devices described in patent FR-2 586 913 in the name of the Applicant.

Using this device, it is possible to dye the keratin fibres from a method which comprises mixing a dyeing composition in accordance with the invention with an oxidizing agent as defined above, and applying the resulting mixture to the keratin fibres for a time sufficient for the desired coloration to develop.

The examples which follow serve to illustrate the invention, but without having any limiting character.

EXAMPLES

Examples of Synthesis

Synthesis of 2-(6-nitro-2,3-dihydro-1H-indol-1-yl)ethyl methanesulphonate, Common to All the Examples

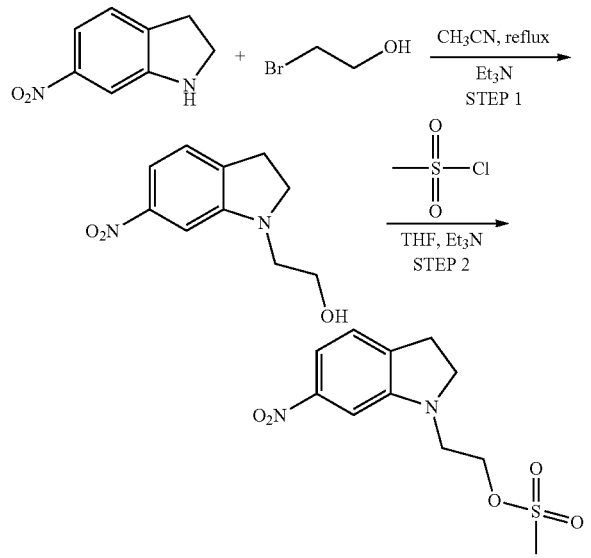

Step 1: Synthesis of 2-(6-nitro-2,3-dihydro-1H-indol-1-yl)ethanol 500 ml of acetonitrile, 50 g (0.304 mol) of 6-nitroindoline, 45.1 ml (1.36 mol) of 2-bromoethanol and 131.5 ml (0.942 mol) of triethylamine are successively charged to a 1 litre three-necked flask equipped with a thermometer, a condenser, a bubbler and a magnetic stirrer, and the mixture is brought to reflux for 24 hours.

The reaction medium is then concentrated under vacuum to 1/10 until a red oil is obtained, which is taken up with 600 ml of dichloromethane. The resulting organic phase is washed with 4×300 ml of water and dried over sodium sulphate $Na_2SO_4$. The dichloromethane is eliminated in a rotary evaporator until a dark red solid having a mass of 64.83 g is obtained, which is purified by silica column chromatography (eluent=90/10 chloroform/methanol) to give 41.13 g (yield 64.8%) of a dark red solid corresponding to the expected product.

Analysis by mass spectrometry confirms the structure of the expected compound: the quasi-molecular ions $[M^+H]^+$, $[M^+Na]^+[M^+Na^+CH_3OH]^+$, $[2M^+Na]^+$, $[M^-H]^-$ of the expected molecule $C_{10}H_{12}N_2O_3$ are mainly detected.

Step 2: Synthesis of 2-(6-nitro-2,3-dihydro-1H-indol-1-yl)ethyl methanesulphonate common to all the examples 150 ml of tetrahydrofuran, 15 g (72.03 mmol) of 2-(6-nitro-2,3-dihydro-1H-indol-1-yl)ethanol and 11.05 ml (79.24 mmol) of triethylamine are successively charged to a 0.5 litre three-necked flask equipped with a thermometer, a condenser, a bubbler, a magnetic stirrer and an isobaric dropping funnel.

This reaction medium is cooled to zero degrees with stirring, and 6.14 ml (79.24 mmol) of methanesulphonyl chloride are added dropwise in order to keep the temperature below 20° C.

Once the dropping is complete, stirring is maintained for 2 hours. The reaction medium is concentrated under vacuum until an orange dry extract is obtained, which is taken up with 150 ml of dichloromethane and 75 ml of water. The organic phase is washed with 2×75 ml of water, dried over sodium sulphate, and concentrated under vacuum until an orange solid, having a mass of 20.43 g, corresponding to the expected compound, is obtained.

Analysis by spectrometry confirms the structure of the expected compound: the quasi-molecular ions $[M^+H]^+$, $[M^+Na]^+[2M^+Na]^+$, of the expected molecule $C_{11}H_{14}N_2O_5S$ are mainly detected.

Example 1

Synthesis of 2-(6-amino-2,3-dihydro-1H-indol-1-yl)-N,N,N-trimethylethanammonium chloride hydrochloride

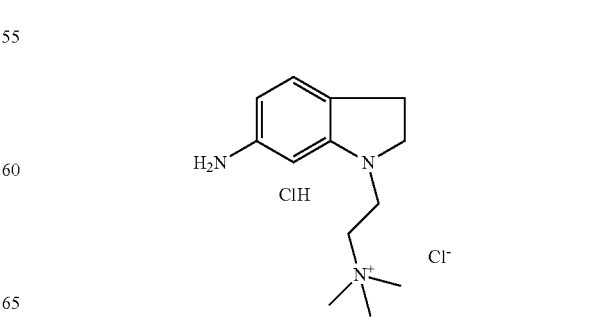

Synthesis of N,N-dimethyl-2-(6-nitro-2,3-dihydro-1H-indol-1-yl)ethanamine

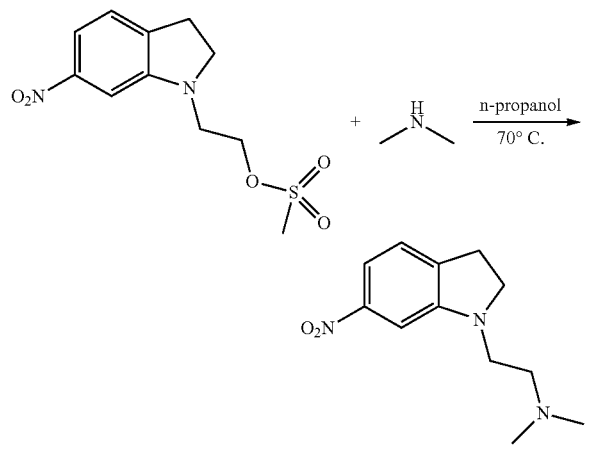

25 ml of propanol, 5 g (17.46 mmol) of 2-(6-nitro-2,3-dihydro-1H-indol-1-yl)ethyl methanesulphonate and 26.2 ml (52.39 mmol) of dimethylamine at 2.0M in MeOH are successively charged to a 100 ml three-necked flask equipped with a thermometer, a condenser, a bubbler and a magnetic stirrer, and the mixture is brought to reflux for 2 hours.

The reaction medium is then concentrated under vacuum to 1/10 until an orange oil is obtained, which is taken up with 250 ml of dichloromethane. 100 ml of 1N sodium hydroxide and 2×100 ml of water are added to the resulting organic phase, and the resulting product is dried over sodium sulphate $Na_2SO_4$.

The dichloromethane is eliminated in a rotary evaporator until an orange oil, having a mass of 3.50 g (yield 85.3%), corresponding to the expected product, is obtained.

Analysis by mass spectrometry confirms the structure of the expected compound: the quasi-molecular ion $[M^+H]^+$ of the expected molecule is detected, as is the fragment ion $[C_{10}H_{11}N_2O_2]^+$ (m/z, ESP+=191).

N,N,N-Trimethyl-2-(6-nitro-2,3-dihydro-1H-indol-1-yl)ethanammonium methyl sulphate

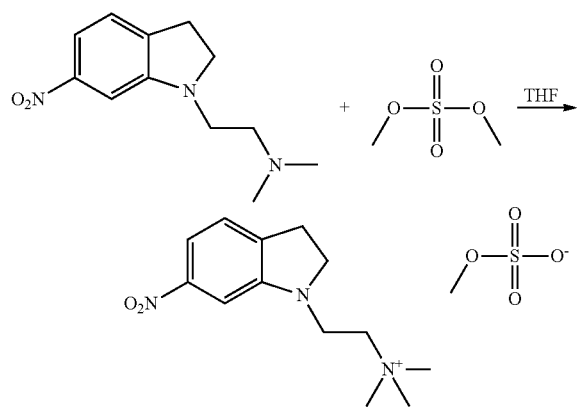

40 ml of tetrahydrofuran and 5 g (17.46 mmol) of N,N-dimethyl-2-(6-nitro-2,3-dihydro-1H-indol-1-yl)ethanamine are successively charged to a 100 ml three-necked flask equipped with a thermometer, a condenser, a bubbler and a magnetic stirrer, and then 2.96 ml (3.12 mmol) of dimethyl sulphate are added dropwise using a syringe.

The reaction medium becomes heterogeneous owing to precipitation of the expected compound. The orange solid formed is isolated by filtration under argon, followed by washing with 50 ml of tetrahydrofuran and then 3×150 ml of 2-propanol.

The solid is then dried under vacuum at 50° C. in the presence of dessecant until the mass is constant. 4.90 g (yield 91.2%) of orange solid corresponding to the expected compound are thus obtained.

Analysis by mass spectrometry confirms the structure of the expected compound: the quasi-molecular ion $[M^+H]^+$ and also the fragment ion $[C_{13}H_{20}N_3O_2]$ of the expected molecule are mainly detected.

Synthesis of 2-(6-amino-2,3-dihydro-1H-indol-1-yl)-N,N,N-trimethylethanammonium chloride hydrochloride

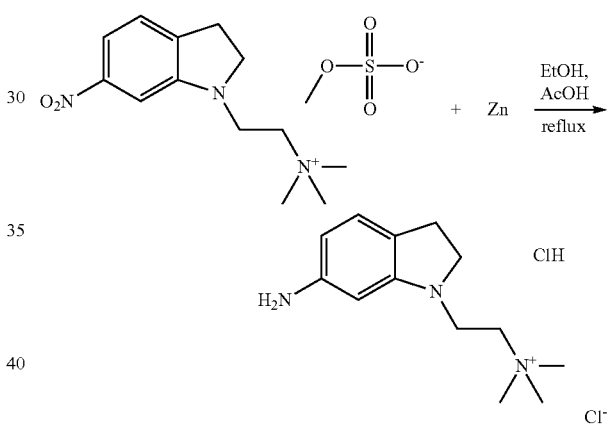

30 ml of ethanol, 2.7 g of zinc powder and 2.1 microlitres of acetic acid are successively charged to a 100 ml three-necked flask equipped with a thermometer, a condenser, a bubbler and a magnetic stirrer, and the medium is brought to reflux.

2.7 g (7.34 mmol) of N,N,N-trimethyl-2-(6-nitro-2,3-dihydro-1H-indol-1-yl)ethanammonium methyl sulphate are added in small spatula-tipfuls.

At the end of addition, the reflux is maintained for 3 hours under argon, and the reaction medium is filtered on a sinter funnel packed with celite and a vacuum flask containing 20 ml of a 6.0N solution of hydrochloric acid containing 2-propanol at 0° C. The zinc is rinsed with a minimum amount of ethyl ether.

With stirring, the expected compound crystallizes in the vacuum flask in the form of a beige solid. The solid is filtered on a sinter funnel, rapidly dried by suction and under argon, and rinsed with a minimum amount of cold iPrOH and then with 3×100 ml of $iPr_2O$. The compound is dried under vacuum at 50° C. in the presence of dessecant, to constant weight. 3.44 g (yield 93.4%) of beige solid corresponding to the expected compound are thus isolated.

Example 2

Synthesis of 1-[2-(6-amino-2,3-dihydro-1H-indol-1-yl)ethyl]-3-methyl-1H-imidazol-3-ium chloride hydrochloride

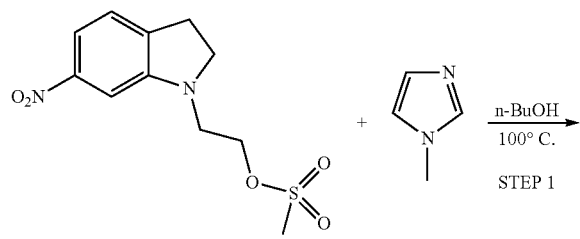

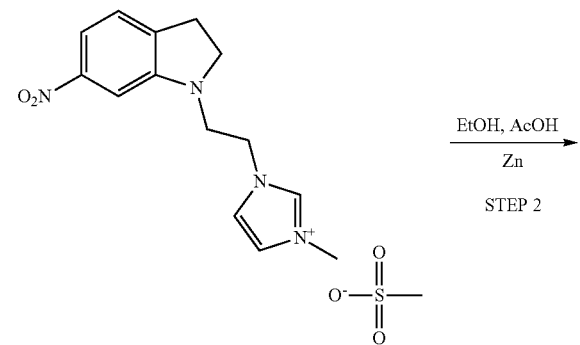

Step 1: Synthesis of 3-methyl-1-[2-(6-nitro-2,3-dihydro-1H-indol-1-yl)ethyl]-1H-imidazol-3-ium methanesulphonate

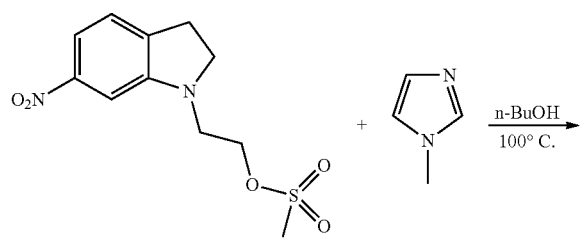

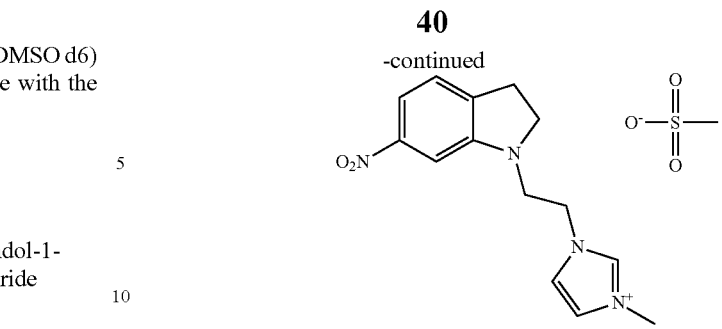

30 ml of n-butanol, 2.70 g (9.43 mmol) of 2-(6-nitro-2,3-dihydro-1H-indol-1-yl)ethyl methanesulphonate and 1.5 ml (18.86 mmol) of 1-methylimidazole are successively charged to a 100 ml three-necked flask equipped with a thermometer, a condenser, a bubbler and a magnetic stirrer, and the mixture is brought to 100° C. for 2 hours.

The reaction mixture is heterogeneous and then homogeneous. After cooling to ambient temperature, the reaction medium is concentrated under vacuum to ¹/₁₀ until an orange oil is obtained, which is taken up with 5 ml of 2-propanol, and an orangey-yellow solid precipitates when ethyl ether is added.

The solid is dried by suction on a sinter funnel, washed with 2×50 ml of diethyl ether, rapidly dried by suction under argon (hygroscopic product) and then dried under vacuum at 50° C. in the presence of dessecant, to constant weight.

2.2 g (yield 63.4%) of expected compound are thus isolated in the form of an orangey-yellow solid.

Mass spectrometry analysis confirms the structure of the expected compound. The expected cation $[C_{14}H_{17}N_4O_2]^+$ is detected at m/z, ESP+=273.

Step 2: Synthesis of 1-[2-(6-amino-2,3-dihydro-1H-indol-1-yl)ethyl]-3-methyl-1H-imidazol-3-ium chloride hydrochloride

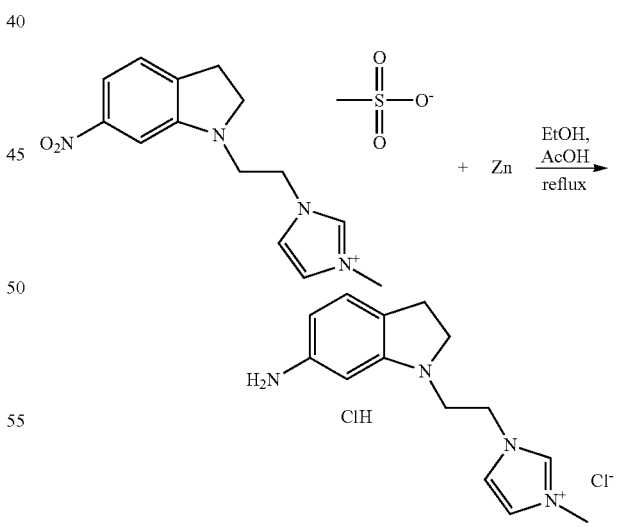

40 ml of ethanol, 4 g of zinc powder and 112 microlitres of acetic acid are successively charged to a 100 ml three-necked flask equipped with a thermometer, a condenser, a bubbler and a magnetic stirrer, and the medium is brought to reflux.

2.20 g (19.65 mmol) of 3-methyl-1-[2-(6-nitro-2,3-dihydro-1H-indol-1-yl)ethyl]-1H-imidazol-3-ium methanesulphonate are added in small spatula-tipfuls.

At the end of addition, the reflux is maintained for 3 hours under argon, and the reaction medium is filtered on a sinter funnel packed with celite and a vacuum flask containing 25 ml of a 6.0N solution of hydrochloric acid containing 2-propanol at 0° C. The zinc is rinsed with a minimum amount of ethyl ether.

With stirring, the expected compound crystallizes in the vacuum flask in the form of a beige solid. The solid is filtered on a sinter funnel, rapidly dried by suction and under argon, and rinsed with a minimum amount of cold iPrOH and then with 3×100 ml of iPr$_2$O. The compound is dried under vacuum at 50° C. in the presence of dessecant, to constant weight. 1.66 g of beige solid corresponding to the expected compound are thus isolated.

The NMR (1H 400 MHz and 13C 100.61 MHz DMSO d6) and mass spectrometry analyses are in accordance with the expected structure.

Example 3

Synthesis of 4-[2-(6-amino-2,3-dihydro-1H-indol-1-yl)ethyl]-1,1-dimethylpiperazin-1-ium chloride hydrochloride

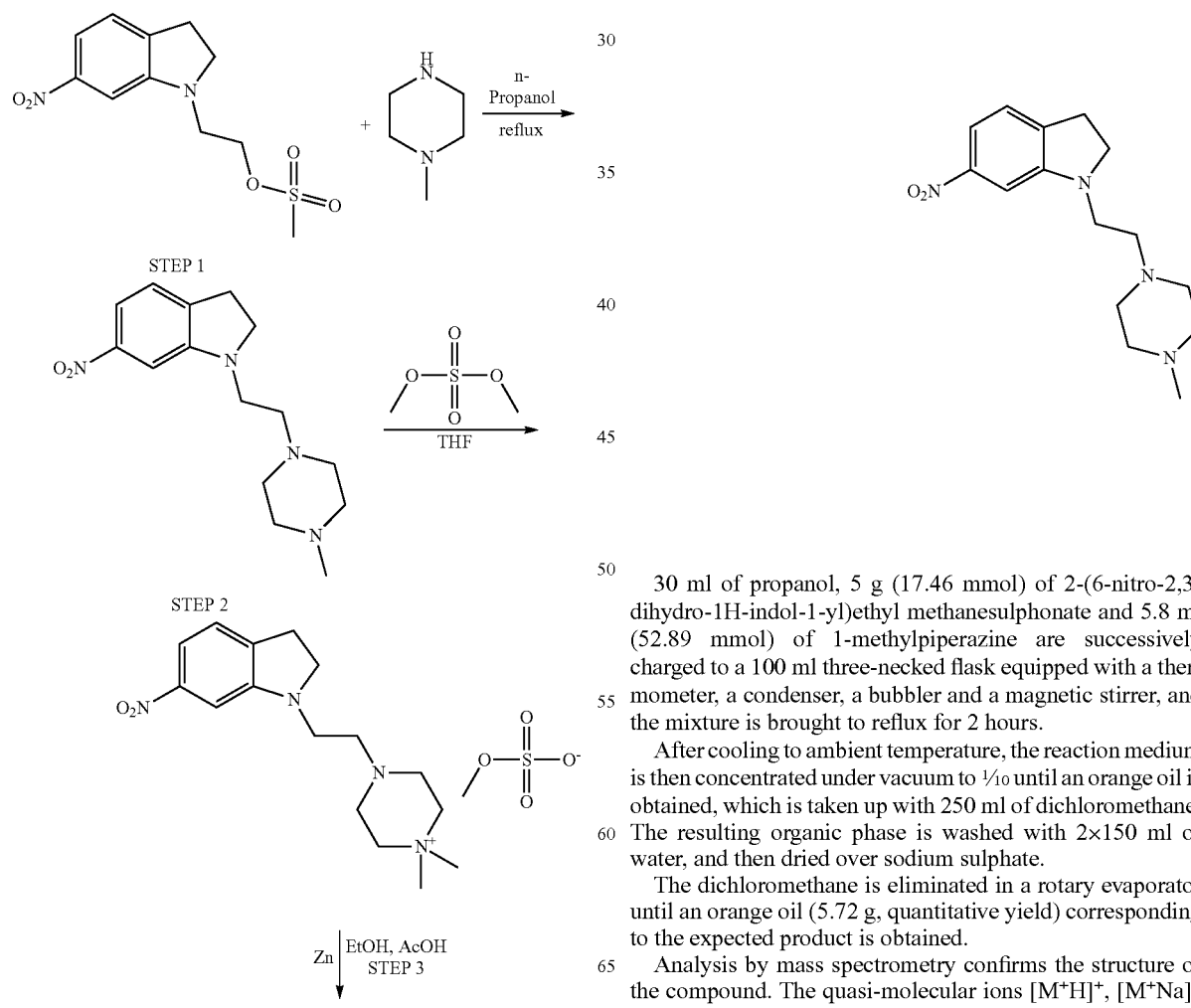

Step 1: Synthesis of 1-[2-(4-methylpiperazin-1-yl)ethyl]-6-nitro-2,3-dihydro-1H-indole

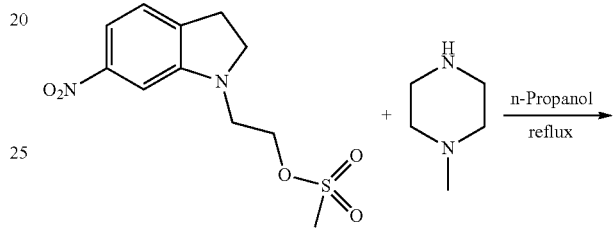

30 ml of propanol, 5 g (17.46 mmol) of 2-(6-nitro-2,3-dihydro-1H-indol-1-yl)ethyl methanesulphonate and 5.8 ml (52.89 mmol) of 1-methylpiperazine are successively charged to a 100 ml three-necked flask equipped with a thermometer, a condenser, a bubbler and a magnetic stirrer, and the mixture is brought to reflux for 2 hours.

After cooling to ambient temperature, the reaction medium is then concentrated under vacuum to ¹/₁₀ until an orange oil is obtained, which is taken up with 250 ml of dichloromethane. The resulting organic phase is washed with 2×150 ml of water, and then dried over sodium sulphate.

The dichloromethane is eliminated in a rotary evaporator until an orange oil (5.72 g, quantitative yield) corresponding to the expected product is obtained.

Analysis by mass spectrometry confirms the structure of the compound. The quasi-molecular ions [M⁺H]⁺, [M⁺Na]⁺ of the expected molecule are mainly detected.

Step 2: Synthesis of 1,1-dimethyl-4-[2-(6-nitro-2,3-dihydro-1H-indol-1-yl)ethyl]piperazin-1-ium methyl sulphate

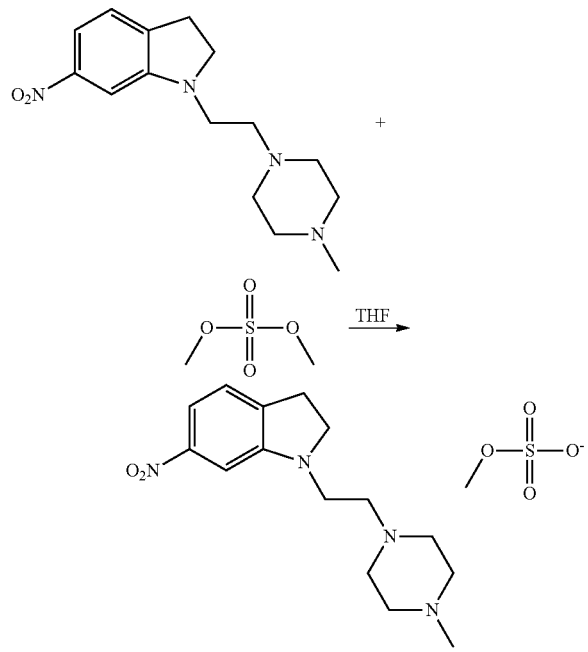

60 ml of tetrahydrofuran and 5.7 g (19.69 mol) of 1-[2-(4-methylpiperazin-1-yl)ethyl]-6-nitro-2,3-dihydro-1H-indole are successively charged to a 100 ml three-necked flask equipped with a thermometer, a condenser, a bubbler and a magnetic stirrer. After cooling to 0° C., 3.9 ml (41.27 mmol) of dimethyl sulphate are added dropwise using a syringe.

An orange solid rapidly precipitates, and the stirring is maintained at ambient temperature for 2 hours.

The solid formed is filtered off on a sinter funnel, dried by suction under argon, and washed with 2×120 ml of tetrahydrofuran and then 3×100 ml of 2-propanol (always under argon since the product is hygroscopic). The orange solid is dried under vacuum at 50° C. in the presence of dessecant, to constant weight. 5.86 g (yield 71.6%) of expected compound are thus isolated.

Analysis by mass spectrometry confirms the structure of the expected compound. The expected cation is detected, as is the counterion $CH_3OSO_3^-$.

Step 3: Synthesis of 4-[2-(6-amino-2,3-dihydro-1H-indol-1-yl)ethyl]-1,1-dimethylpiperazin-1-ium chloride hydrochloride

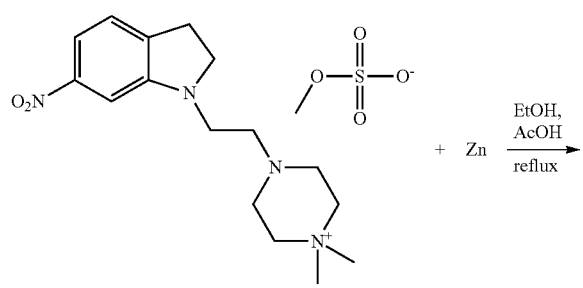

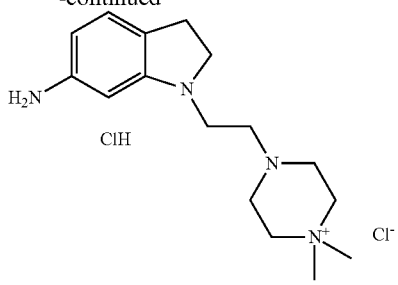

40 ml of ethanol, 4 g of zinc powder and 112 microlitres of acetic acid are successively charged to a 100 ml three-necked flask equipped with a thermometer, a condenser, a bubbler and a magnetic stirrer, and the medium is then brought to reflux.

4 g (19.65 mmol) of 1,1-dimethyl-4-[2-(6-nitro-2,3-dihydro-1H-indol-1-yl)ethyl]piperazin-1-ium methyl sulphate are added in small spatula-tipfuls.

At the end of addition, the reflux is maintained for 3 hours under argon, and the reaction medium is filtered on a sinter funnel packed with celite and a vacuum flask containing 25 ml of a 6.0N solution of hydrochloric acid containing 2-propanol at 0° C. The zinc is rinsed with a minimum amount of 2-propanol.

With stirring, the expected compound crystallizes in the vacuum flask in the form of a beige solid. The solid is rapidly filtered on a sinter funnel and under argon, dried by suction, and rinsed with a minimum amount of cold 2-propanol and then with 3×100 ml of ethyl ether. The compound is dried under vacuum at 50° C. in the presence of dessecant, to constant weight.

3.57 g (yield 99.7%) of beige solid corresponding to the expected compound are thus isolated.

The NMR (1H 400 MHz and 13C 100.61 MHz DMSO d6) and mass spectrometry analyses are in accordance with the expected structure.

Examples of Dyeing

The following dyeing compositions are prepared

| Example | 1 | 2 | 3 |
|---|---|---|---|
| 2,3-Diamino-6,7-dihydro-1H,5H-pyrazolo[1,2-a]pyrazol-1-one dimethanesulphonate | $10^{-3}$ mol | $10^{-3}$ mol | $10^{-3}$ mol |
| 2-(6-Amino-2,3-dihydro-1H-indol-1-yl)-N,N,N-trimethylethanammonium chloride hydrochloride | $10^{-3}$ mol | — | — |
| 1-[2-(6-Amino-2,3-dihydro-1H-indol-1-yl)ethyl]-3-methyl-1H-imidazol-3-ium chloride hydrochloride | — | $10^{-3}$ mol | — |
| 4-[2-(6-Amino-2,3-dihydro-1H-indol-1-yl)ethyl]-1,1-dimethylpiperazin-1-ium chloride hydrochloride | — | — | $10^{-3}$ mol |
| Dyeing support | (1) | (1) | (1) |
| Demineralized water qs | 100 g | 100 g | 100 g |
| Shade observed | Strong chromatic coppery red | Strong brick red | Strong chromatic coppery red |

-continued

| Example | 4 | 5 | 6 |
|---|---|---|---|
| 2-[(3-Aminopyrazolo[1,5-a]pyridin-2-yl)oxy]ethanol hydrochloride | $10^{-3}$ mol | $10^{-3}$ mol | $10^{-3}$ mol |
| 2-(6-Amino-2,3-dihydro-1H-indol-1-yl)-N,N,N-trimethylethanammonium chloride hydrochloride | $10^{-3}$ mol | — | — |
| 1-[2-(6-Amino-2,3-dihydro-1H-indol-1-yl)ethyl]-3-methyl-1H-imidazol-3-ium chloride hydrochloride | — | $10^{-3}$ mol | — |
| 4-[2-(6-Amino-2,3-dihydro-1H-indol-1-yl)ethyl]-1,1-dimethylpiperazin-1-ium chloride hydrochloride | — | — | $10^{-3}$ mol |
| Dyeing support | (1) | (1) | (1) |
| Demineralized water qs | 100 g | 100 g | 100 g |
| Shade observed | Strong chromatic violet | Strong violet | Strong chromatic violet |

| Example | 7 | 8 | 9 |
|---|---|---|---|
| 4-(3-Aminopyrazolo[1,5-a]pyridin-2-yl)-1,1-dimethylpiperazin-1-ium chloride hydrochloride | $10^{-3}$ mol | $10^{-3}$ mol | $10^{-3}$ mol |
| 2-(6-Amino-2,3-dihydro-1H-indol-1-yl)-N,N,N-trimethylethanammonium chloride hydrochloride | $10^{-3}$ mol | — | — |
| 1-[2-(6-Amino-2,3-dihydro-1H-indol-1-yl)ethyl]-3-methyl-1H-imidazol-3-ium chloride hydrochloride | — | $10^{-3}$ mol | — |
| 4-[2-(6-Amino-2,3-dihydro-1H-indol-1-yl)ethyl]-1,1-dimethylpiperazin-1-ium chloride hydrochloride | — | — | $10^{-3}$ mol |
| Dyeing support | (1) | (1) | (1) |
| Demineralized water qs | 100 g | 100 g | 100 g |
| Shade observed | Strong chromatic green | Strong green | Strong chromatic green |

| Example | 10 | 11 | 12 |
|---|---|---|---|
| 2-[{2-[(4-Aminophenyl)amino]ethyl}(2-hydroxyethyl)amino]ethanol hydrochloride | $10^{-3}$ mol | $10^{-3}$ mol | $10^{-3}$ mol |
| 2-(6-Amino-2,3-dihydro-1H-indol-1-yl)-N,N,N-trimethylethanammonium chloride hydrochloride | $10^{-3}$ mol | — | — |
| 1-[2-(6-Amino-2,3-dihydro-1H-indol-1-yl)ethyl]-3-methyl-1H-imidazol-3-ium chloride hydrochloride | — | $10^{-3}$ mol | — |
| 4-[2-(6-Amino-2,3-dihydro-1H-indol-1-yl)ethyl]-1,1-dimethylpiperazin-1-ium chloride hydrochloride | — | — | $10^{-3}$ mol |
| Dyeing support | (1) | (1) | (1) |
| Demineralized water qs | 100 g | 100 g | 100 g |
| Shade observed | Strong matt grey | Strong matt grey | Matt grey |

| Example | 13 | 14 | 15 |
|---|---|---|---|
| 4-Aminophenylamine dihydrochloride | $10^{-3}$ mol | $10^{-3}$ mol | $10^{-3}$ mol |
| 2-(6-Amino-2,3-dihydro-1H-indol-1-yl)-N,N,N-trimethylethanammonium chloride hydrochloride | $10^{-3}$ mol | — | — |
| 1-[2-(6-Amino-2,3-dihydro-1H-indol-1-yl)ethyl]-3-methyl-1H-imidazol-3-ium chloride hydrochloride | — | $10^{-3}$ mol | — |
| 4-[2-(6-Amino-2,3-dihydro-1H-indol-1-yl)ethyl]-1,1-dimethylpiperazin-1-ium chloride hydrochloride | — | — | $10^{-3}$ mol |
| Dyeing support | (1) | (1) | (1) |
| Demineralized water qs | 100 g | 100 g | 100 g |
| Shade observed | Blue-grey | Matt grey | Dark grey |

| Example | 16 | 17 | 18 |
|---|---|---|---|
| 4-Aminophenol | $10^{-3}$ mol | $10^{-3}$ mol | $10^{-3}$ mol |
| 2-(6-Amino-2,3-dihydro-1H-indol-1-yl)-N,N,N-trimethylethanammonium chloride hydrochloride | $10^{-3}$ mol | — | — |
| 1-[2-(6-Amino-2,3-dihydro-1H-indol-1-yl)ethyl]-3-methyl-1H-imidazol-3-ium chloride hydrochloride | — | $10^{-3}$ mol | — |
| 4-[2-(6-Amino-2,3-dihydro-1H-indol-1-yl)ethyl]-1,1-dimethylpiperazin-1-ium chloride hydrochloride | — | — | $10^{-3}$ mol |
| Dyeing support | (1) | (1) | (1) |
| Demineralized water qs | 100 g | 100 g | 100 g |
| Shade observed | Pearlescent mahogany | Coppery mahogany | Bright chromatic mahogany |

| Example | 19 | 20 | 21 |
|---|---|---|---|
| Compound of sulphuric acid with 2-(4,5-diamino-1H-pyrazol-1-yl)ethanol (1:1) | $10^{-3}$ mol | $10^{-3}$ mol | $10^{-3}$ mol |
| 2-(6-Amino-2,3-dihydro-1H-indol-1-yl)-N,N,N-trimethylethanammonium chloride hydrochloride | $10^{-3}$ mol | — | — |
| 1-[2-(6-Amino-2,3-dihydro-1H-indol-1-yl)ethyl]-3-methyl-1H-imidazol-3-ium chloride hydrochloride | — | $10^{-3}$ mol | — |
| 4-[2-(6-Amino-2,3-dihydro-1H-indol-1-yl)ethyl]-1,1-dimethylpiperazin-1-ium chloride hydrochloride | — | — | $10^{-3}$ mol |
| Dyeing support | (1) | (1) | (1) |
| Demineralized water qs | 100 g | 100 g | 100 g |
| Shade observed | Bright and chromatic violet | Bright and chromatic blue-violet | Bright and chromatic raspberry |

(1): Dyeing Support at pH 9.5:

| | |
|---|---|
| 96° ethyl alcohol | 20.8 g |
| 35% aqueous sodium metabisulphite solution | 0.23 g a.s. |
| 40% aqueous solution of the pentasodium salt of diethylene-triaminepentaacetic acid | 0.48 g a.s. |
| 60% aqueous solution of $C_8$-$C_{10}$ alkyl polyglucoside | 3.6 g a.s. |
| Benzyl alcohol | 2.0 g |
| Polyethylene glycol containing 8 ethylene oxide units | 3.0 g |
| NH4Cl | 4.32 g |
| Aqueous ammonia containing 20% of $NH_3$ | 2.94 g | where a.s. signifies "active substance"

At the time of use, each composition is mixed with an equal weight of 20-volumes hydrogen peroxide (6% by weight). A final pH of 9.5 is obtained.

Each mixture obtained is applied to locks of grey hair containing 90% white hairs. After a leave-in time of 30 minutes, the locks are rinsed, washed with a standard shampoo, rinsed again and then dried, to give the shades mentioned.

The invention claimed is:

1. Cationic 6-aminoindoline of general formula (I), addition salts thereof with an acid and solvates thereof:

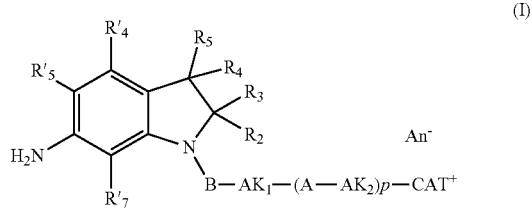

in which:
B denotes a covalent bond or a carbonyl radical CO;
$AK_1$ and $AK_2$ independently denote a linear or branched, saturated $C_1$-$C_{10}$ hydrocarbon-based chain optionally substituted with one or more hydroxyl radicals;
A denotes an oxygen atom or an $NR_6$ radical;
p=0, 1 or 2;
when p is equal to 2, the A radicals may be identical or different and the $AK_2$ radicals may be identical or different;
$R_2$, $R_3$, $R_4$ and $R_5$, independently of one another, are selected from: a hydrogen atom, halogens selected from fluorine, chlorine or bromine, and linear or branched $C_1$-$C_4$ alkyl, carboxyl (—COOH), ($C_1$-$C_4$)alkoxycarbonyl, $C_1$-$C_4$ hydroxyalkyl or ($C_1$-$C_4$)alkoxy($C_1$-$C_4$)alkyl radicals;
$R'_4$, $R'_5$ and $R'_7$, independently of one another, are selected from: a hydrogen atom, halogens selected from fluorine, chlorine or bromine, and $C_1$-$C_4$ alkyl radicals;
$R_6$ is a hydrogen atom or a linear or branched $C_1$-$C_4$ alkyl radical, a $C_1$-$C_4$ hydroxyalkyl radical, a benzyl radical or an acetyl radical,
$CAT^+$ represents a cationic radical selected from:
  a cationic heterocyclic radical optionally substituted with one or more radicals, which may be identical or different, selected from linear or branched $C_1$-$C_4$ alkyl radicals or linear or branched $C_1$-$C_4$ hydroxylalkyl radicals,
  a tri(hydroxy)($C_1$-$C_4$)alkylammonium radical,
  a non-cationic heterocyclic radical comprising from 5 to 8 ring members, substituted with a cationic radical optionally substituted with one or more radicals, which may be identical or different, selected from linear or branched $C_1$-$C_4$ alkyl radicals or $C_1$-$C_4$ hydroxyalkyl radicals;
$An^-$ represents a cosmetically acceptable organic or mineral anion or a mixture of cosmetically acceptable organic or mineral anions.

2. Cationic 6-aminoindoline according to claim 1, in which the cationic radical is a tri(hydroxy)($C_1$-$C_4$)alkylammonium radical selected from trimethylammonium, triethylammonium, dimethylethylammonium, diethylmethylammonium, diisopropylmethylammonium, diethylpropylammonium, beta-hydroxyethyldiethylammonium, dimethyl-beta-hydroxyethylammonium, di-beta-hydroxyethylmethylammonium and tri-beta-hydroxyethylammonium radicals.

3. Cationic 6-aminoindoline according to claim 1, in which the cationic radical is a cationic heterocyclic radical selected from imidazolium, pyridinium, piperazinium, pyrrolidinium, morpholinium, pyrimidinium, thiazolium, benzimidazolium, benzothiazolium, oxazolium, benzotriazolium, pyrazolium, triazolium, benzoxazolium and piperidinium radicals.

4. Cationic 6-aminoindoline according to claim 1, in which B represents a covalent bond or a carbonyl radical CO, $AK_1$ represents a saturated linear $C_1$-$C_4$ hydrocarbon-based chain, p is equal to 0, and $CAT^+$ is selected from imidazolium, piperazinium, pyrrolidinium, morpholinium or piperidinium radicals, optionally substituted with a $C_1$-$C_2$ alkyl radical; the following radicals: piperidine, pyrrolidine, morpholine, substituted with a methyltrimethylammonium, methyldiethylmethylammonium, methyl(N-methylpyrrolidinium) or trimethylammonium radical; and trimethylammonium, triethylammonium or dimethyl-beta-hydroxyethylammonium radicals.

5. Cationic 6-aminoindoline according to claim 1, in which B represents a covalent bond or a carbonyl radical CO, $AK_1$ represents a saturated linear $C_1$-$C_4$ hydrocarbon-based chain, p is equal to 1, A represents an oxygen atom or an NH radical and $CAT^+$ is selected from imidazolium, piperazinium, pyrrolidinium, morpholinium or piperidinium radicals, optionally substituted with a $C_1$-$C_2$ alkyl radical; the following radicals: piperidine, pyrrolidine, morpholine, piperidine substituted with a methyltrimethylammonium, methyldimethylethylammonium, methyl(N-methylpyrrolidinium) or trimethylammonium radical; and trimethylammonium, triethylammonium or dimethyl-beta-hydroxyethylammonium radicals.

6. Cationic 6-aminoindoline according to claim 1, in which $R_2$, $R_3$, $R_4$ and $R_5$, independently of one another, are selected from a hydrogen atom and $C_1$-$C_4$ alkyl radicals.

7. Cationic 6-aminoindoline according to claim 1, in which $R'_4$, $R'_5$ and $R'_7$, are identical and represent hydrogen atoms.

8. Cationic 6-aminoindoline according to claim 1, in which $R_6$ is a hydrogen atom.

9. Cationic 6-aminoindoline according to claim 1, as selected from the following compounds:

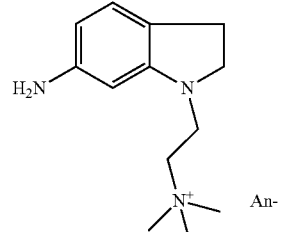

2-(6-Amino-2,3-dihydro-1H-indol-1-yl)-N,N,N-trimethylethanammonium, An-

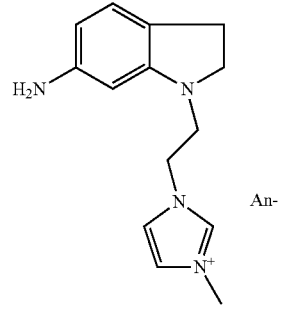

1-[2-(6-Amino-2,3-dihydro-1H-indol-1-yl)ethyl]-3-methyl-1H-imidazol-3-ium, An-

-continued

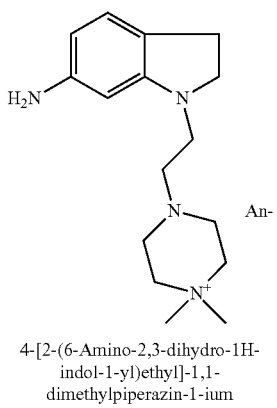

4-[2-(6-Amino-2,3-dihydro-1H-
indol-1-yl)ethyl]-1,1-
dimethylpiperazin-1-ium

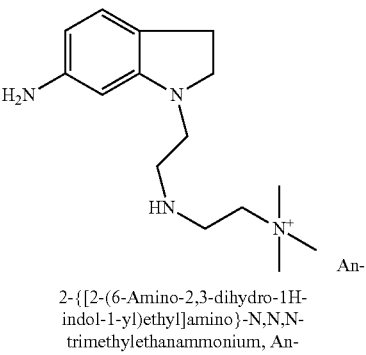

2-{[2-(6-Amino-2,3-dihydro-1H-
indol-1-yl)ethyl]amino}-N,N,N-
trimethylethanammonium, An-

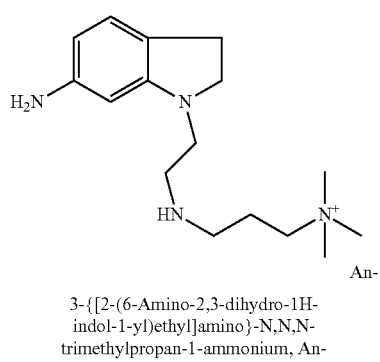

3-{[2-(6-Amino-2,3-dihydro-1H-
indol-1-yl)ethyl]amino}-N,N,N-
trimethylpropan-1-ammonium, An-

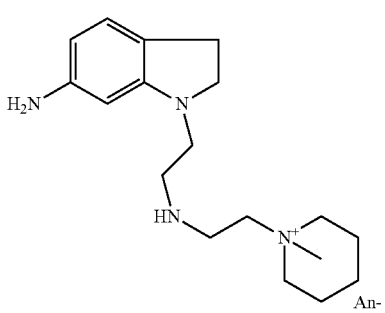

1-(2-{[2-(6-Amino-2,3-dihydro-1H-
indol-1-yl)ethyl]amino}ethyl)-1-
methylpiperidinium, An- -continued

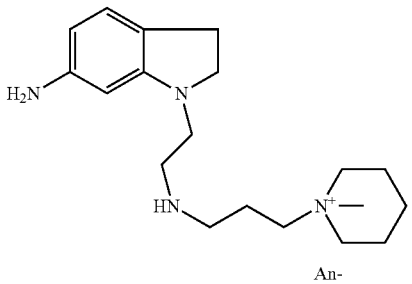

1-(3-{[2-(6-Amino-2,3-dihydro-1H-
indol-1-yl)ethyl]amino}propyl)-1-
methylpiperidinium, An-

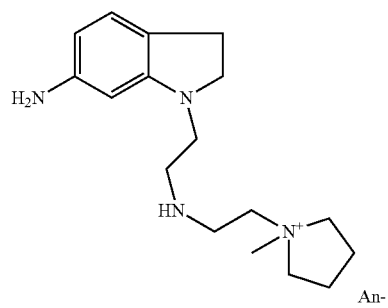

1-(2-{[2-(6-Amino-2,3-dihydro-1H-
indol-1-yl)ethyl]amino}ethyl)-1-
methylpyrrolidinium, An-

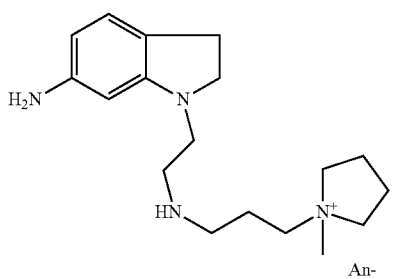

1-(3-{[2-(6-Amino-2,3-dihydro-1H-
indol-1-yl)ethyl]amino}propyl)-1-
methylpyrrolidinium, An-

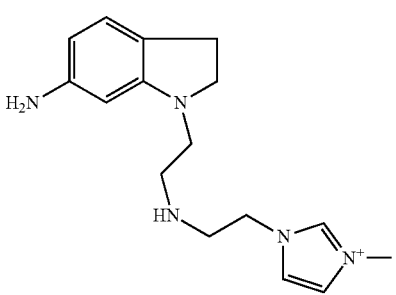

1-(2-{[2-(6-Amino-2,3-dihydro-1H-
indol-1-yl)ethyl]amino}ethyl)-3-
methyl-1H-imidazol-3-ium, An-

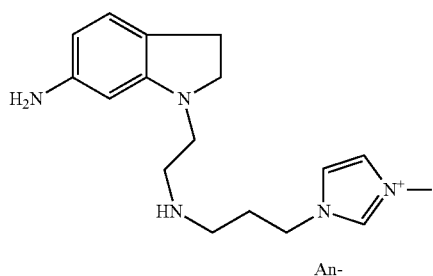

1-(3-{[2-(6-Amino-2,3-dihydro-1H-
indol-1-yl)ethyl]amino}propyl)-3-
methyl-1H-imidazol-3-ium, An-

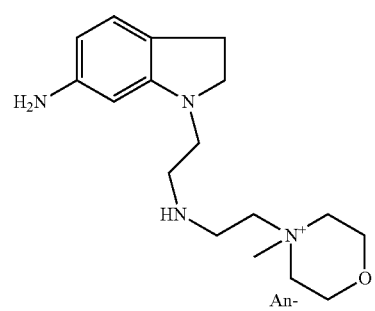

4-(2-{[2-(6-Amino-2,3-dihydro-1H-
indol-1-yl)ethyl]amino}ethyl)-4-
methylmorpholin-4-ium, An-

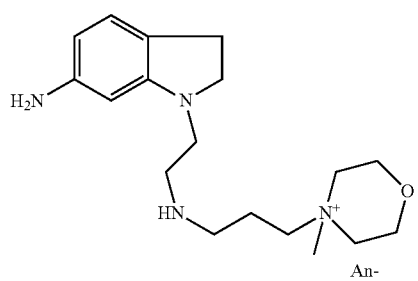

4-(3-{[2-(6-Amino-2,3-dihydro-1H-
indol-1-yl)ethyl]amino}propyl)-4-
methylmorpholin-4-ium, An-

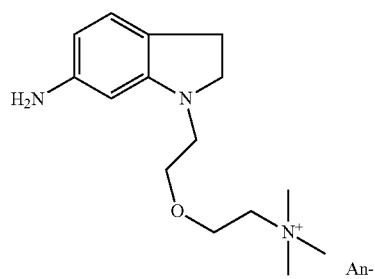

2-[2-(6-Amino-2,3-dihydro-1H-indol-
1-yl)ethoxy]-N,N,N-
trimethylethanammonium, An-

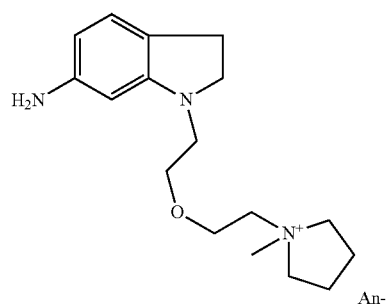

1-{2-[2-(6-Amino-2,3-dihydro-1H-
indol-1-yl)ethoxy]-ethyl}-1-
methylpyrrolidinium, An-

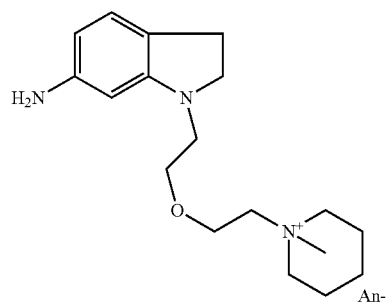

1-{2-[2-(6-Amino-2,3-dihydro-1H-
indol-1-yl)ethoxy]ethyl}-1-
methylpiperidinium, An-

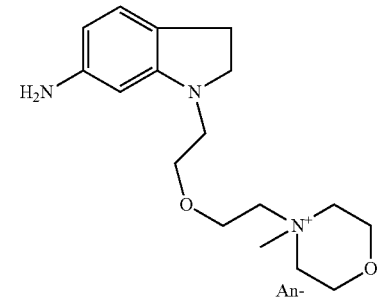

4-{2-[2-(6-Amino-2,3-dihydro-1H-
indol-1-yl)ethoxy]ethyl}-4-
methylmorpholin-4-ium, An-

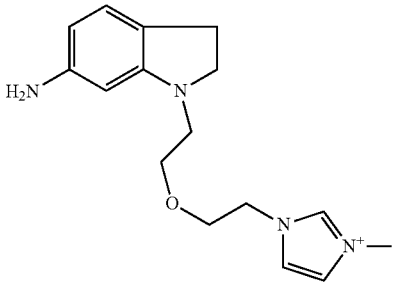

1-{2-[2-(6-Amino-2,3-dihydro-1H-
indol-1-yl)ethoxy]ethyl}-3-methyl-
1H-imidazol-3-ium, An-

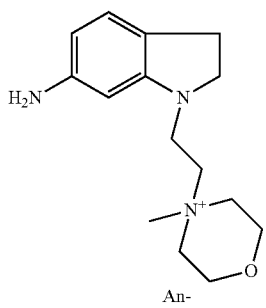

4-[2-(6-Amino-2,3-dihydro-1H-
indol-1-yl)ethyl]-4-
methylmorpholin-4-ium, An-

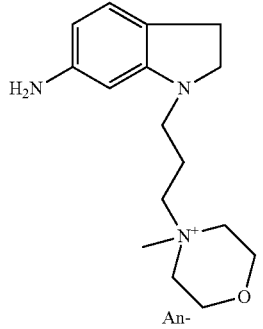

4-[3-(6-Amino-2,3-dihydro-1H-indol-
1-yl)propyl]-4-methylmorpholin-4-ium, An-

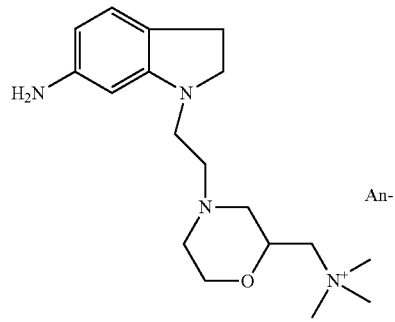

{4-[2-(6-Amino-2,3-dihydro-1H-
indol-1-yl)ethyl]morpholin-2-yl}-
N,N,N-trimethylmethanammonium,
An-

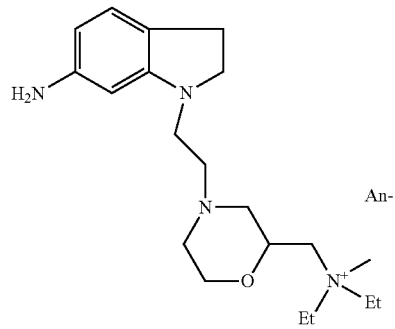

{4-[2-(6-Amino-2,3-dihydro-1H-
indol-1-yl)ethyl]morpholin-2-yl}N-
methyl-N,N-diethyl-
methanammonium, An-

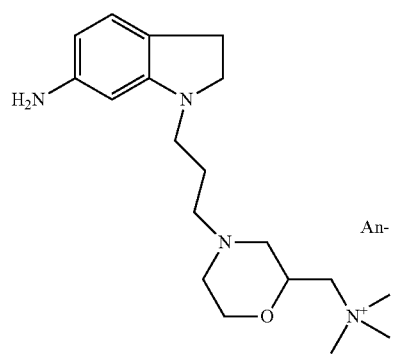

{4-[3-(6-Amino-2,3-dihydro-1H-
indol-1-yl)propyl]morpholin-2-yl}-
N,N,N-trimethylmethanammonium,
An-

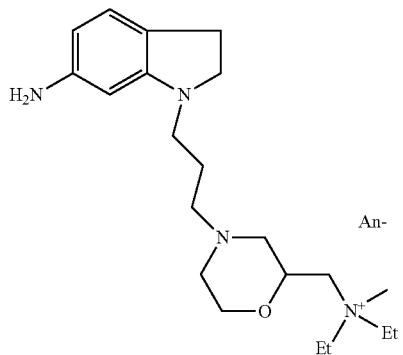

{4-[3-(6-Amino-2,3-dihydro-1H-
indol-1-yl)propyl]morpholin-2-
yl}N-methyl-N,N-diethyl-
methanammonium, An-

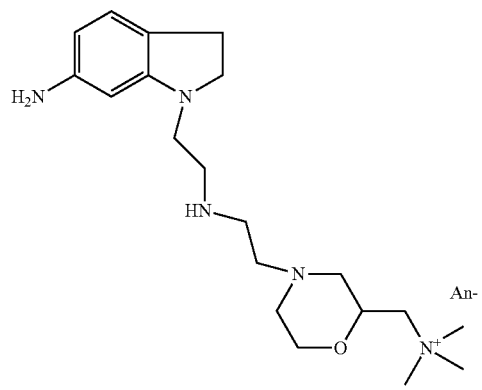

[4-(2-{[2-(6-Amino-2,3-dihydro-1H-
indol-1-yl)ethyl]amino}ethyl)-
morpholin-2-yl]-N,N,N-
trimethylmethanammonium, An-

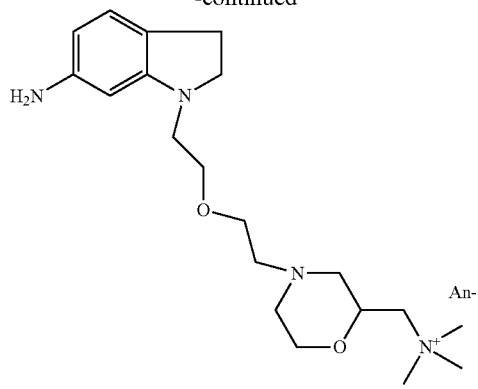

(4-{2-[2-(6-Amino-2,3-dihydro-1H-
indol-1-yl)ethoxy]ethyl}morpholin-
2-yl)-N,N,N-
trimethylmethanammonium, An-

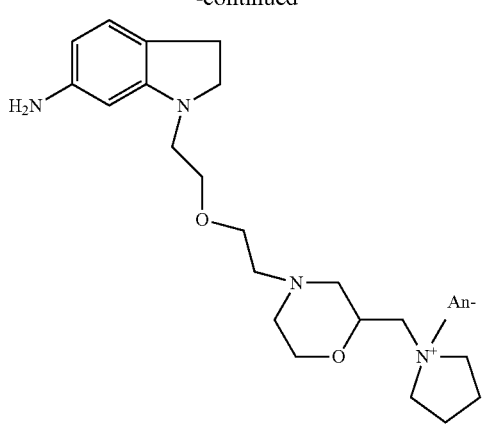

1-[(4-{2-[2-(6-Amino-2,3-dihydro-
1H-indol-1-yl)ethoxy]ethyl}-
morpholin-2-yl)-methyl]-1-
methylpyrrolidinium, An-

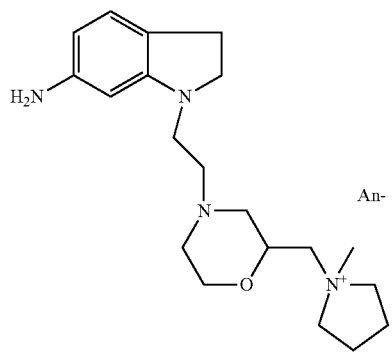

1-({4-[2-(6-Amino-2,3-dihydro-1H-
indol-1-yl)ethyl]morpholin-2-
yl}methyl)-1-methylpyrrolidinium,
An-

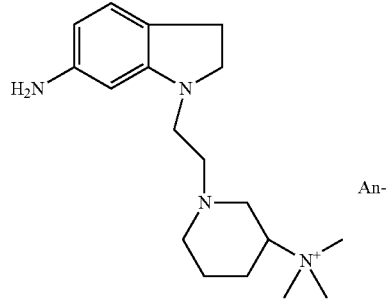

1-[2-(6-Amino-2,3-dihydro-1H-
indol-1-yl)ethyl]-N,N,N-
trimethylpiperidin-3-ammonium,
An-

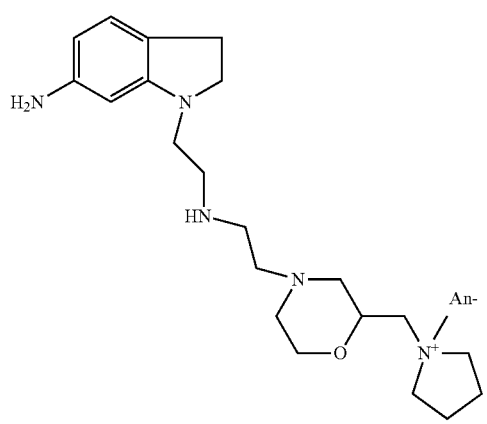

1-{[4-(2-{[2-(6-Amino-2,3-dihydro-
1H-indol-1-yl)ethyl]amino}ethyl)-
morpholin-2-yl]-methyl}-1-
methylpyrrolidinium, An-

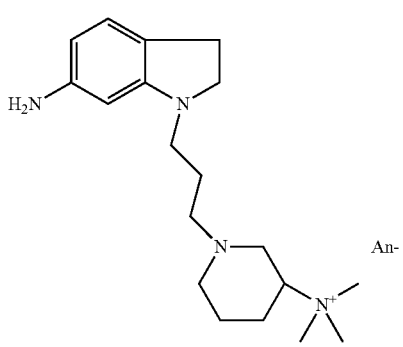

1-[3-(6-Amino-2,3-dihydro-1H-indol-
1-yl)propyl]-N,N,N-
trimethylpiperidin-3-ammonium, An- -continued

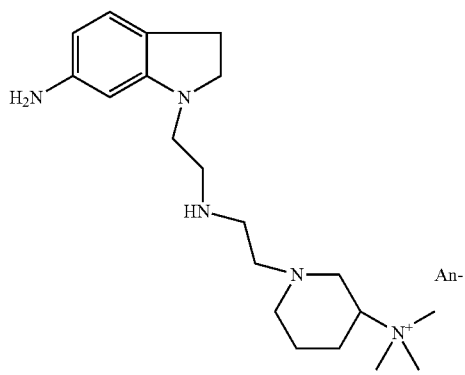

1-(2-{[2-(6-Amino-2,3-dihydro-1H-indol-1-yl)ethyl]amino}ethyl)-N,N,N-trimethylpiperidin-3-ammonium, An-

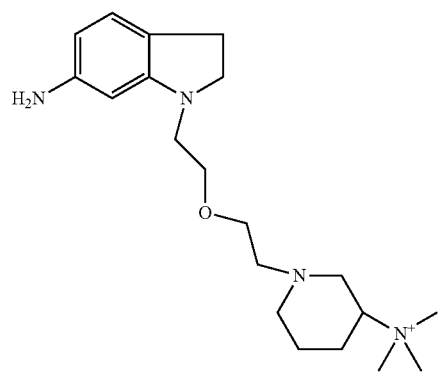

1-{2-[2-(6-Amino-2,3-dihydro-1H-indol-1-yl)ethoxy]ethyl}-N,N,N-trimethylpiperidin-3-ammonium, An-

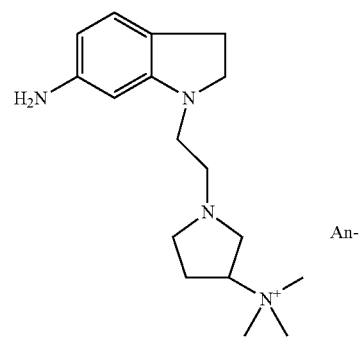

1-[2-(6-Amino-2,3-dihydro-1H-indol-1-yl)ethyl]-N,N,N-trimethylpyrrolidin-3-ammonium, An- -continued

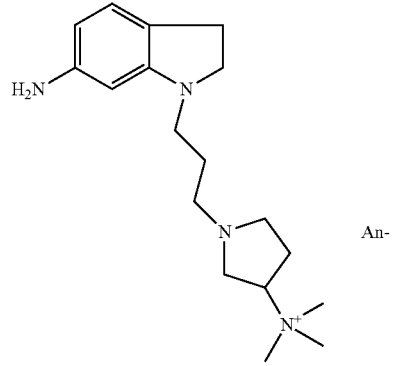

1-[3-(6-Amino-2,3-dihydro-1H-indol-1-yl)propyl]-N,N,N-trimethylpyrrolidin-3-ammonium, An-

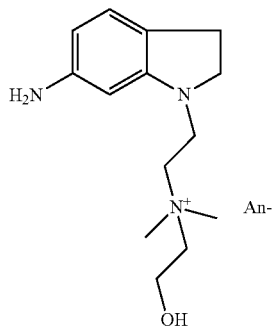

2-(6-Amino-2,3-dihydro-1H-indol-1-yl)-N-(2-hydroxyethyl)-N,N-dimethylethanammonium, An-

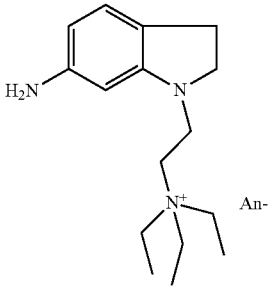

2-(6-Amino-2,3-dihydro-1H-indol-1-yl)-N,N,N-triethylethanammonium, An-

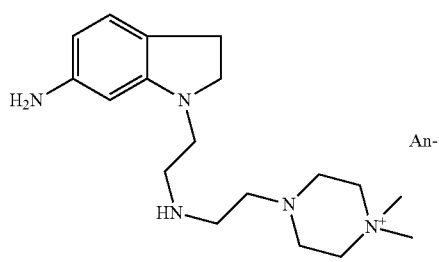

4-(2-{[2-(6-Amino-2,3-dihydro-1H-indol-1-yl)-ethyl]amino}ethyl)-1,1-dimethylpiperazin-1-ium, An-

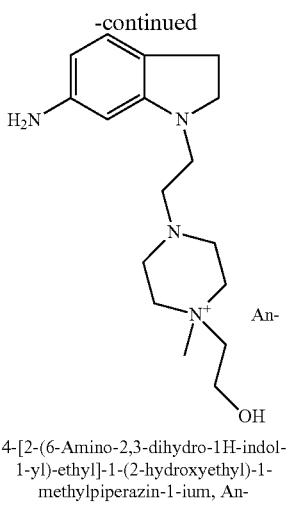

4-[2-(6-Amino-2,3-dihydro-1H-indol-1-yl)-ethyl]-1-(2-hydroxyethyl)-1-methylpiperazin-1-ium, An-

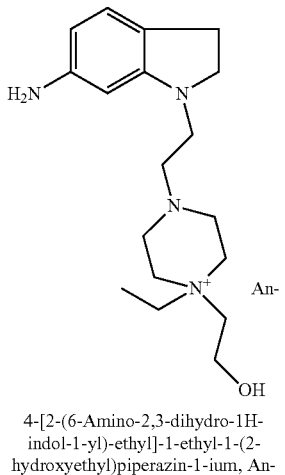

4-[2-(6-Amino-2,3-dihydro-1H-indol-1-yl)-ethyl]-1-ethyl-1-(2-hydroxyethyl)piperazin-1-ium, An-

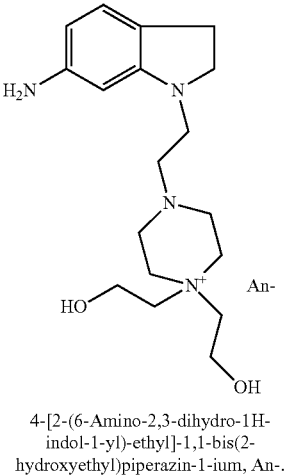

4-[2-(6-Amino-2,3-dihydro-1H-indol-1-yl)-ethyl]-1,1-bis(2-hydroxyethyl)piperazin-1-ium, An-.

10. Method for synthesizing a cationic 6-aminoindoline of general formula (I) as defined in claim 1, starting from an indoline of formula (II):

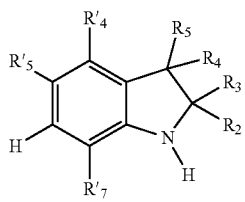

(II)

in which the definitions of the radicals $R_2$, $R_3$, $R_4$, $R_5$, $R'_4$, $R'_5$ and $R'_7$ are those envisaged in claim 1, said method comprising at least the following steps in this order:

nitration of the indoline of formula (II) so as to obtain a nitroindoline, substitution of the hydrogen atom borne by the nitrogen atom with the radical —B-AK$_1$-(A-AK$_2$)$_p$-CAT$^+$ reduction of the nitro group.

11. A composition for dyeing keratin fibers in particular hair, comprising as a coupler, the cationic 6-aminoindoline of a formula (I) as defined in claim 1.

12. Cosmetic dyeing composition comprising, in a medium suitable for dyeing, at least one cationic 6-aminoindoline of formula (I) as defined in claim 1.

13. Composition according to claim 12, characterized in that it is a ready-to-use composition comprising at least one oxidizing agent selected from hydrogen peroxide, urea peroxide, alkali metal bromates, persalts, peracids and oxidase enzymes.

14. Method of dyeing keratin fibres, characterized in that the composition according to claim 12 is applied to said fibres for a time sufficient to develop the desired colouration in the presence of an oxidizing agent, the oxidizing agent being applied before, simultaneously with or after the composition.

15. Multi-compartment device, a first compartment containing the cosmetic composition for dyeing keratin fibres as defined in claim 12 and a second compartment containing an oxidizing agent.

* * * * *